(12) United States Patent
Nishide et al.

(10) Patent No.: US 9,166,173 B2
(45) Date of Patent: Oct. 20, 2015

(54) ORGANIC COMPOUND

(75) Inventors: Yosuke Nishide, Kawasaki (JP); Jun Kamatani, Tokyo (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 412 days.

(21) Appl. No.: 13/698,223

(22) PCT Filed: May 11, 2011

(86) PCT No.: PCT/JP2011/061356
§ 371 (c)(1),
(2), (4) Date: Nov. 15, 2012

(87) PCT Pub. No.: WO2011/145637
PCT Pub. Date: Nov. 24, 2011

(65) Prior Publication Data
US 2013/0056722 A1    Mar. 7, 2013

(30) Foreign Application Priority Data

May 19, 2010    (JP) .................................. 2010-115492

(51) Int. Cl.
| | | |
|---|---|---|
| *C07C 13/62* | (2006.01) | |
| *C07C 211/61* | (2006.01) | |
| *C07D 209/86* | (2006.01) | |
| *C07D 213/06* | (2006.01) | |
| *C07D 401/10* | (2006.01) | |
| *H01L 51/54* | (2006.01) | |
| *H01L 51/00* | (2006.01) | |
| *C07C 211/54* | (2006.01) | |
| *C07C 209/86* | (2006.01) | |
| *C07D 213/53* | (2006.01) | |
| *C09K 11/06* | (2006.01) | |
| *H01L 51/50* | (2006.01) | |

(52) U.S. Cl.
CPC ............ *H01L 51/0056* (2013.01); *C07C 13/62* (2013.01); *C07C 209/86* (2013.01); *C07C 211/54* (2013.01); *C07C 211/61* (2013.01); *C07D 213/06* (2013.01); *C07D 213/53* (2013.01); *C09K 11/06* (2013.01); *C07C 2103/54* (2013.01); *C09K 2211/1011* (2013.01); *C09K 2211/1029* (2013.01); *H01L 51/0058* (2013.01); *H01L 51/5012* (2013.01)

(58) Field of Classification Search
CPC .... C07C 13/62; C07C 103/54; C07C 211/54; C07C 211/61; C07D 209/86; C07D 213/06; C07D 213/53; C09K 11/06; C09K 2211/1011; C09K 2211/1029; H01L 51/0056; H01L 51/0058; H01L 51/5012; H01L 51/54; H05B 33/14

See application file for complete search history.

(56) References Cited

U.S. PATENT DOCUMENTS

| | | | | |
|---|---|---|---|---|
| 7,183,010 | B2 * | 2/2007 | Jarikov | .......................... 428/690 |
| 2002/0168544 | A1 * | 11/2002 | Fukuoka et al. | .............. 428/690 |
| 2014/0231787 | A1 * | 8/2014 | Ishige et al. | ..................... 257/40 |

FOREIGN PATENT DOCUMENTS

| | | |
|---|---|---|
| JP | 2-247278 A | 10/1990 |
| JP | 8-113576 A | 5/1996 |
| JP | 2005-068087 A | 3/2005 |

(Continued)

*Primary Examiner* — Dawn Garrett
(74) *Attorney, Agent, or Firm* — Canon U.S.A. Inc., IP Division

(57) ABSTRACT

A novel organic compound is suitable for emitting green light. An organic light-emitting device includes the novel organic compound.

9 Claims, 1 Drawing Sheet

(56) References Cited

FOREIGN PATENT DOCUMENTS

| JP | 2009-126848 A | 6/2009 |
| JP | 2009-149612 A | 7/2009 |
| JP | 2009-280522 A | 12/2009 |
| JP | 2010-018574 A | 1/2010 |

* cited by examiner

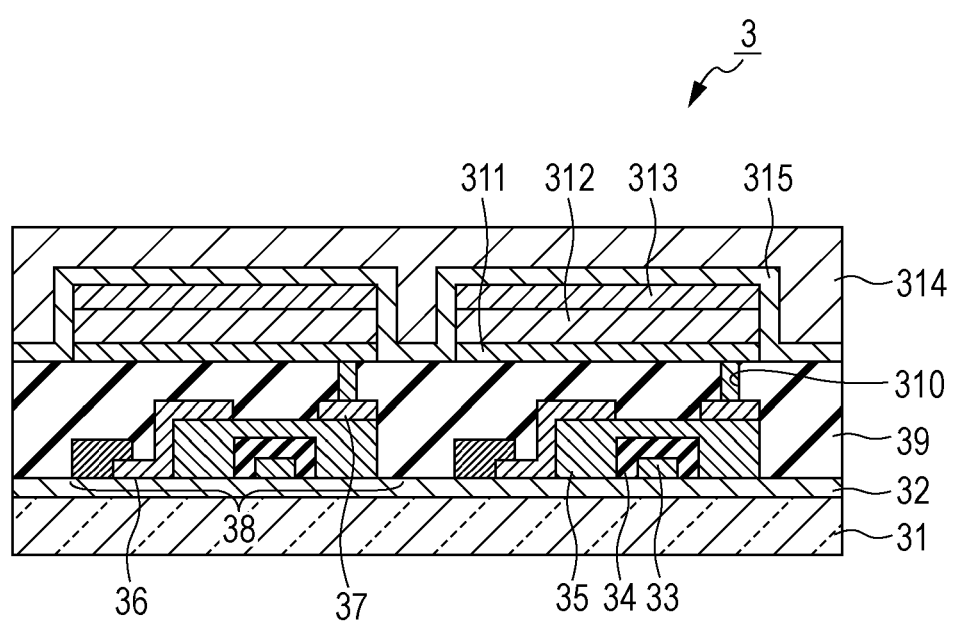

ORGANIC COMPOUND

TECHNICAL FIELD

The present invention relates to a novel organic compound included in an organic light-emitting device and an image display apparatus.

BACKGROUND ART

An organic light-emitting device is a device that includes an anode, a cathode, and an organic compound layer interposed between the anode and the cathode. Holes and electrons injected from the respective electrodes of the organic light-emitting device are recombined in the organic compound layer to generate excitons and light is emitted as the excitons return to their ground state.

The organic light-emitting device is also called an organic electroluminescent device or organic EL device. Recent years have seen remarkable advances in the field of organic light-emitting devices. Organic light-emitting devices offer low driving voltage, various emission wavelengths, rapid response, and small thickness and are light-weight.

Extensive efforts have been made on creation of novel light-emitting organic compounds. Creation of such compounds are critical for producing high-performance organic light-emitting devices.

For example, PTL 1 and 2 disclose examples of the materials used in emission layers. PTL 1 discloses an organic compound represented by the structural formula below:

[Chem. 1]

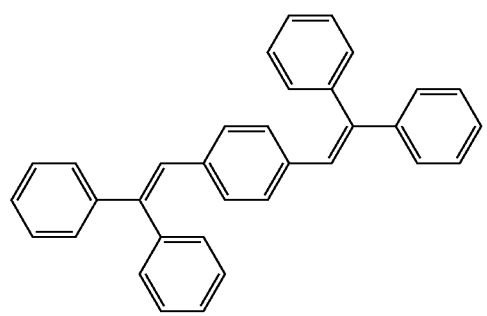

PTL 2 discloses an organic compound represented by a structural formula below:

[Chem. 2]

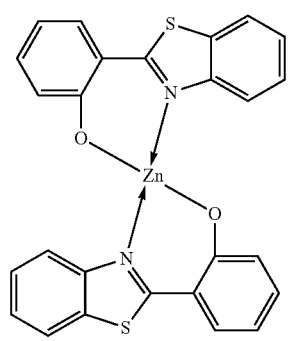

The organic compounds and the organic light-emitting devices described in these patent literatures need to be improved to meet practical needs.

CITATION LIST

Patent Literature

PTL 1 Japanese Patent Laid-Open No. 2-247278
PTL 2 Japanese Patent Laid-Open No. 8-113576

SUMMARY OF INVENTION

The present invention provides a novel organic compound that has a basic skeleton itself capable of achieving emission in a green range. The novel organic compound is represented by general formula (1):

[Chem. 3]

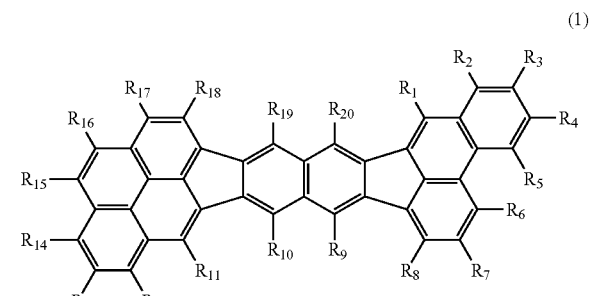

(1)

In formula (1), $R_1$ to $R_{20}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group, and substituents of the alkyl group, the alkoxy group, the amino group, the aryl group, and the heterocyclic group are each individually selected from an alkyl group, an aralkyl group, an aryl group, a heterocyclic group, an amino group, an alkoxyl group, and a halogen atom.

BRIEF DESCRIPTION OF DRAWINGS

FIG. 1 is a schematic diagram showing an organic light-emitting device and a switching element connected to the organic light-emitting device.

DESCRIPTION OF EMBODIMENTS

First, a novel organic compound according to an embodiment of the present invention is described. The organic compound is represented by general formula (1) below:

[Chem. 4]

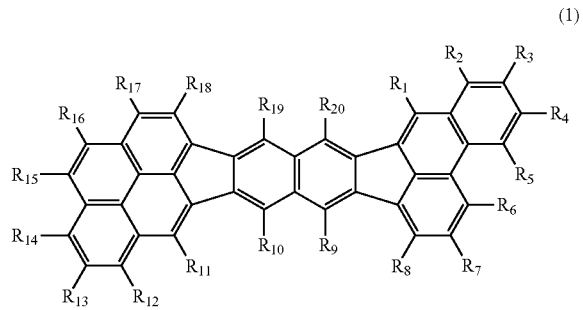

(1)

In general formula (1), $R_1$ to $R_{20}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group. These substituents may include substituents.

Examples of the alkyl group include, but are not limited to, a methyl group, an ethyl group, a normal propyl group, an isopropyl group, a normal butyl group, a secondary butyl group, a tertiary butyl group, an octyl group, a 1-adamantyl group, and 2-adamantyl group.

Examples of the alkoxy group include, but are not limited to, a methoxy group, an ethoxy group, a propoxy group, a 2-ethyl-octyloxy group, a phenoxy group, a 4-tertiary butylphenoxy group, a benzyloxy group, and a thienyloxy group.

Examples of the amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tertiary butylphenyl)amino group, and an N-phenyl-N-(4-trifluoromethylphenyl)amino group.

Examples of the aryl group include, but are not limited to, a phenyl group, a naphthyl group, an indenyl group, a biphenyl group, a terphenyl group, and a fluorenyl group.

Examples of the heterocyclic group include, but are not limited to, a pyridyl group, an oxazolyl group, an oxadiazolyl group, a thienyl group, a thiazolyl group, a thiadiazolyl group, a carbazolyl group, an acridinyl group, and a phenanthrolyl group.

Examples of the substituents to be included in the substituents described above, i.e., the alkyl group, the alkoxy group, the amino group, the aryl group, and the heterocyclic group, include, but are not limited to, alkyl groups such as a methyl group, an ethyl group, and a propyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, a propoxyl group, and a phenoxyl group; a cyano group; and halogen atoms such as fluorine, chlorine, bromine, and iodine.

The inventors have focused on the basic skeleton of the compound. In particular, the basic skeleton has following two properties.

First, the emission wavelength of a molecule containing only the basic skeleton is within the desired emission wavelength range and the emission quantum yield is high. In general, in order to increase the emission efficiency of organic light-emitting devices, the emission quantum yield of the emission center material itself is desirably high.

For the purposes of the present invention, the desired emission wavelength range refers to a green range, i.e., in the range of 480 nm to 530 nm. Although a substituent may be introduced into the basic skeleton to obtain a desired emission wavelength, this may destabilize the compound.

When the skeleton that contributes to emission is free of any substituent, i.e., a rotatable structure, the decrease in quantum yield caused by vibration resulting from rotation can be suppressed.

The organic compound of the embodiment of the present invention has no rotatable structure despite that the maximum emission wavelength of the basic skeleton is within the green range. Thus, the decrease in quantum yield caused by rotation vibration can be suppressed.

Comparison with Other Organic Compounds

The organic compound of the embodiment will now be compared with a similar compound, benzo[k]fluoranthene.

[Chem. 5]

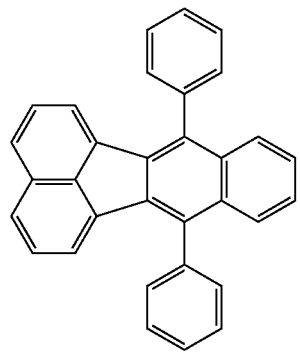

7,12-Diphenylbenzo[k]fluoranthene

[Chem. 6]

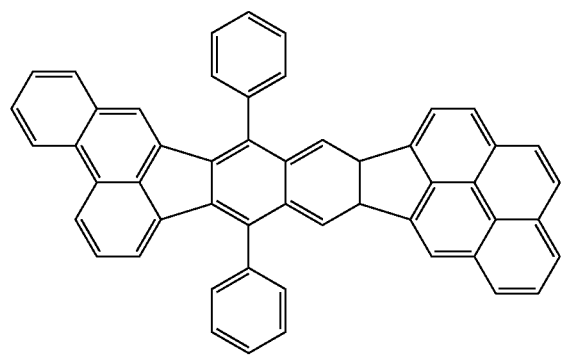

Compound 1

One example of the structure that can function as the basic skeleton is benzo[k]fluoranthene. The maximum emission wavelength is compared between the organic compound of the embodiment (compound 1) and 7,12-diphenylbenzo[k]fluoranthene, which is benzo[k]fluoranthene with phenyl groups substituting the 7- and 12-positions. Whereas the maximum emission length of 7,12-diphenylbenzo[k]fluoranthene is 428 nm, that of the compound of the embodiment is about 485 nm. This suggests that compound 1 emits light in the green range merely by having a fused ring structure.

This shows that the compound of the embodiment has emission suitable for emitting green light solely by having the basis skeleton and achieves a high quantum yield.

Second, since the organic compound of the embodiment has two 5-membered ring structures within the skeleton, the HOMO-LUMO energy level is lowered and the organic compound is stable against oxidation.

That the HOMO-LUMO energy level is lowered means that the oxidation potential is also lowered. This means that it takes more energy to oxidize the compound, i.e., the compound is more stable against oxidation.

Thus, the organic compound of the embodiment having two 5-membered ring structures within the skeleton has a low HOMO-LUMO energy level and oxidation potential and is stable against oxidation.

The organic compound of the embodiment has no heteroatoms such as nitrogen atoms in the basic skeleton. This also contributes to lowering the oxidation potential and renders the organic compound more stable against oxidation.

When the organic compound is used as an emission material, it may be used as an electron-trap-type emission material. An organic light-emitting device includes at least one organic compound layer between a pair of electrodes. The organic compound of the embodiment is to be contained in this at least one organic compound layer.

The organic compound of the embodiment may be used as a guest or host material of an emission layer of an organic light-emitting device. It may also be used in any layers other than the emission layer, namely, a hole injection layer, a hole transport layer, a hole/exciton blocking layer, an electron transport layer, and an electron injection layer.

The organic compound of the embodiment may be used as a guest material of an emission layer of an organic light-emitting device. It may be used as a guest material of a green light-emitting device.

The organic compound of the embodiment may be used as a red light-emitting material by introducing a substituent that provides a longer emission wavelength into the basic skeleton. The material having the longer wavelength is also stable against oxidation since the basic skeleton is the same as that of the organic compound of the embodiment.

Examples of the substituent that provides longer emission wavelengths include an aryl group and a triarylamino group.

The organic compound may be used as a guest material of the emission layer and a material having a higher LUMO than the organic compound, in other words, a material closer to the vacuum level than the organic compound, may be used as a host material. This is because the organic compound of the embodiment having a low LUMO can smoothly receive electrons, that have been supplied to the emission layer or the host material, from the host material.

Since the basic skeleton of the organic compound of the embodiment itself has a wide band gap, it can be used as a host material of a yellow or red emission layer.

A host material is the material having the largest weight ratio among the compounds constituting the emission layer. A guest material is a material having a weight ratio smaller than that of the host material among the compound constituting the emission layer.

The host and guest materials are described in further detail below. The organic compound of the embodiment may be used as a guest material of an emission layer of an organic light-emitting device. As a result, an organic light-emitting device that emits green light can be provided.

Examples of the Organic Compound of the Embodiment

Non-limiting examples of the compound represented by general formula (1) are provided below.

[Chem. 7]

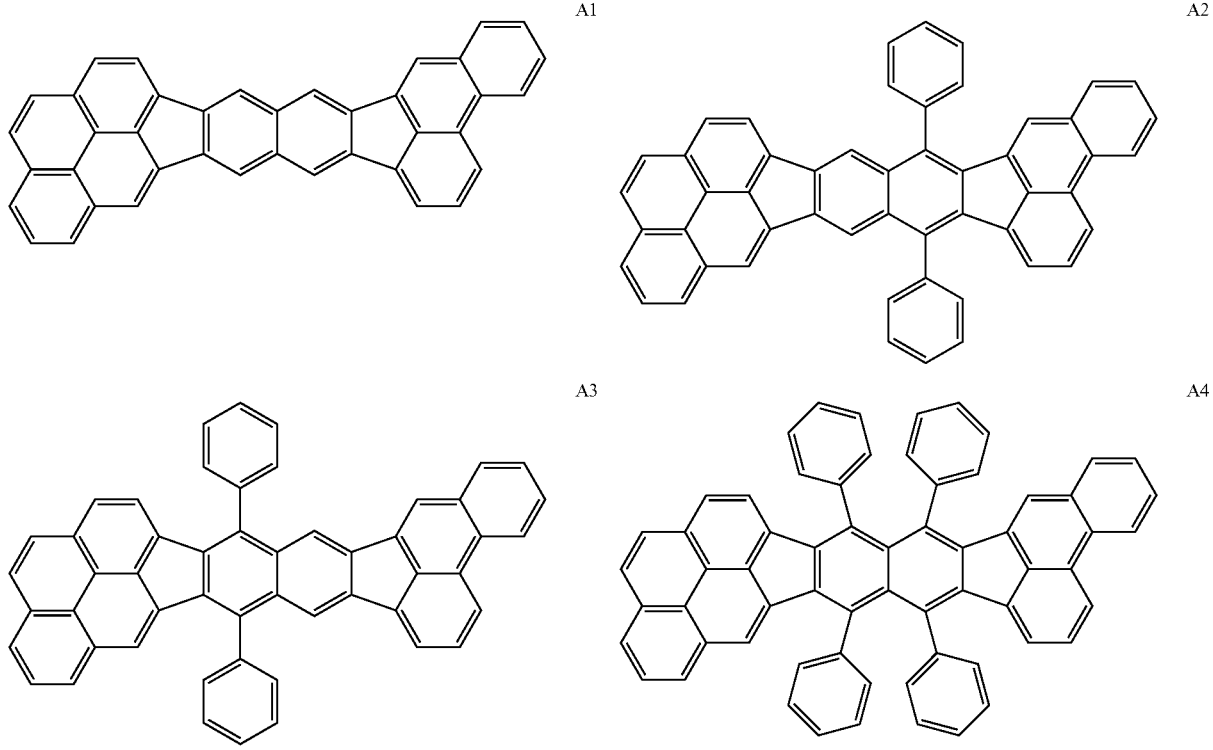

-continued
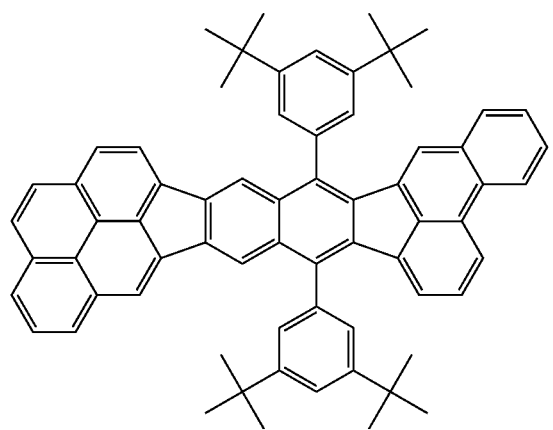
A5
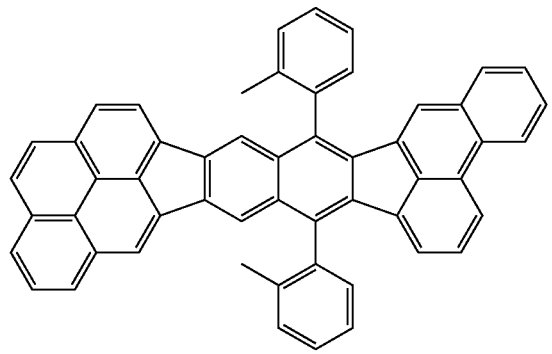
A6
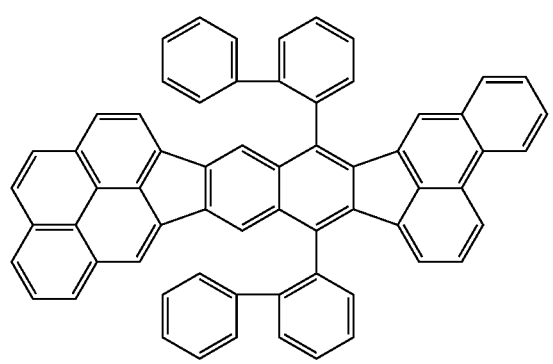
A7
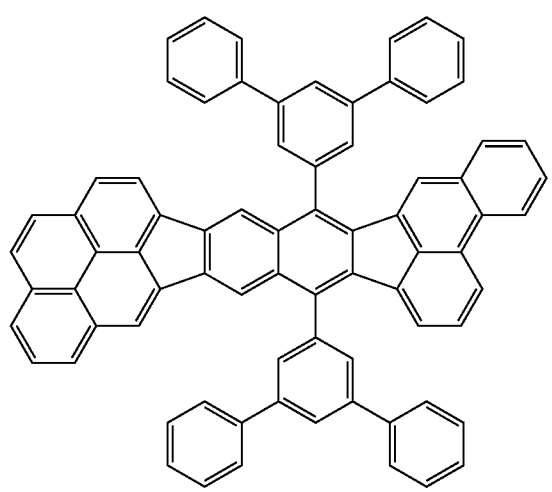
A8
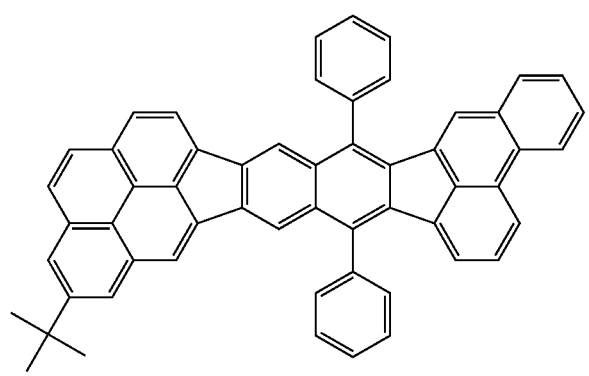
A9
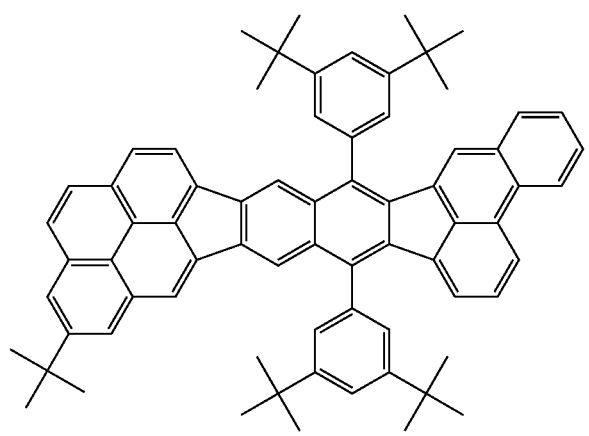
A10

-continued
A11
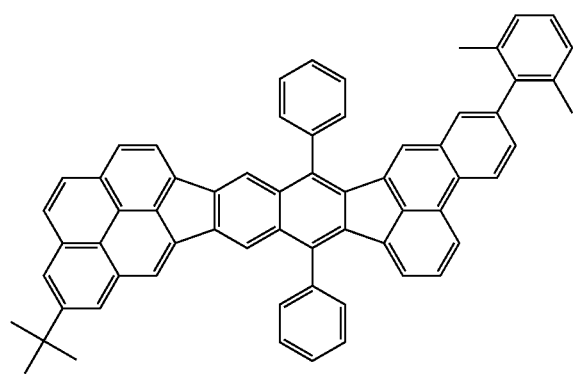
A12
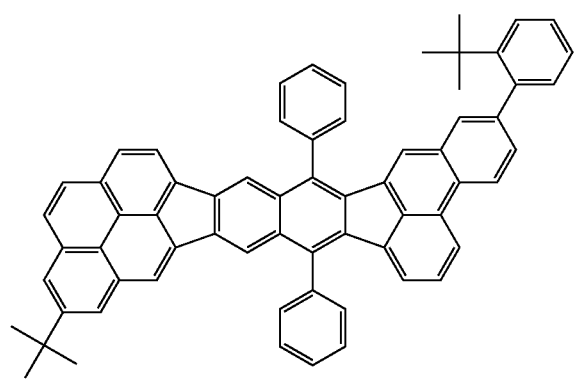
A13
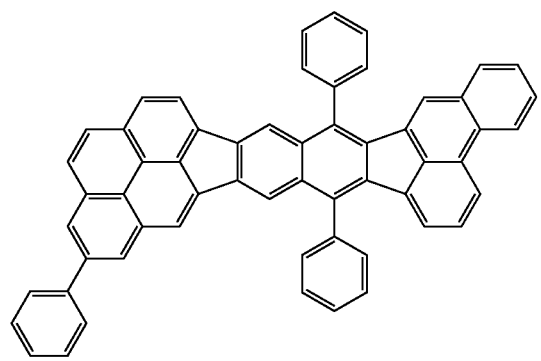
A14
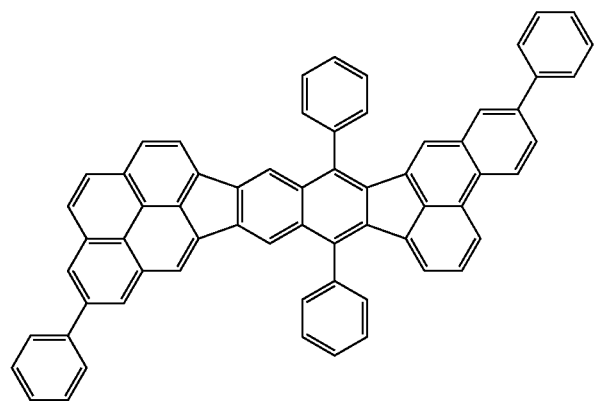
A15
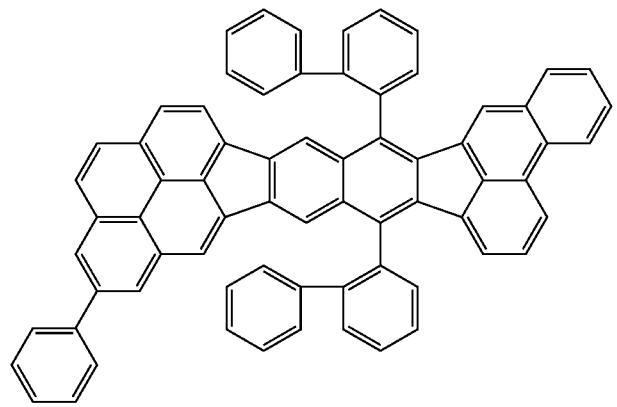

[Chem. 8]
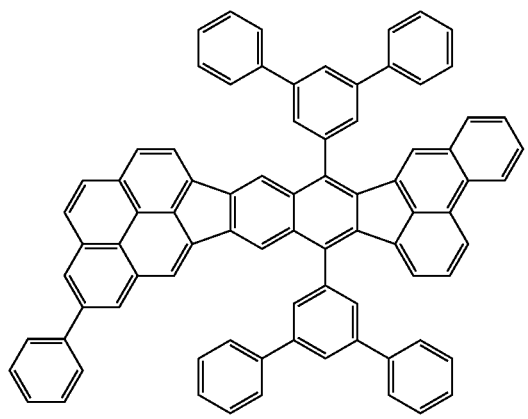
A16
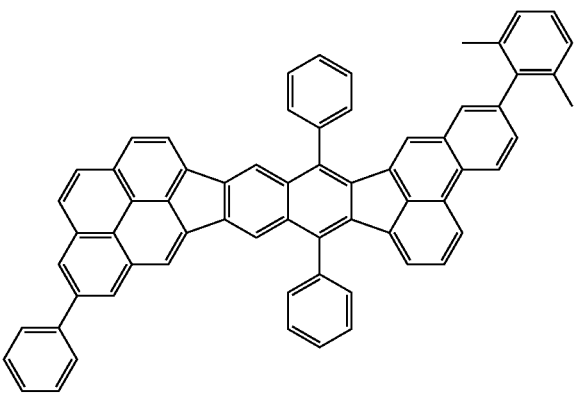
A17
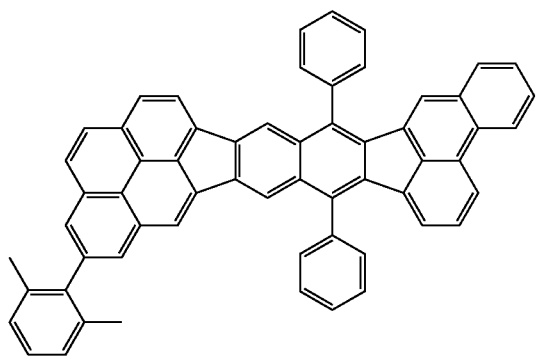
A18
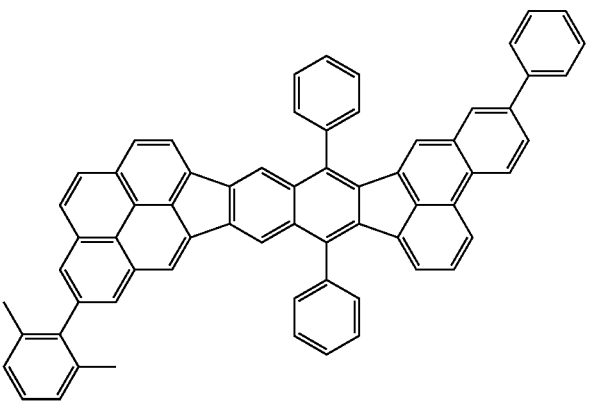
A19
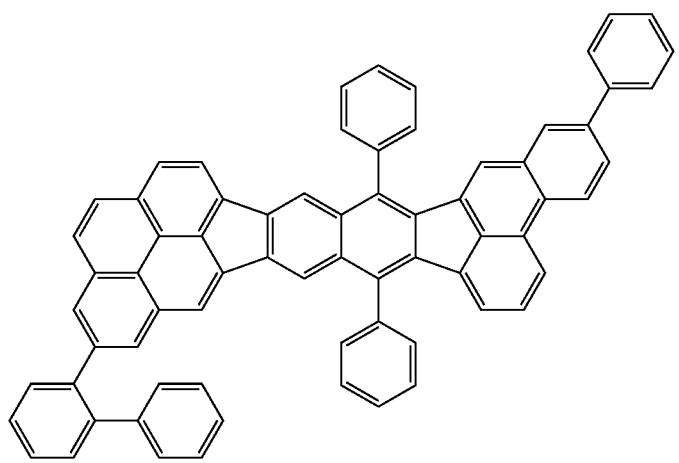
A20

-continued
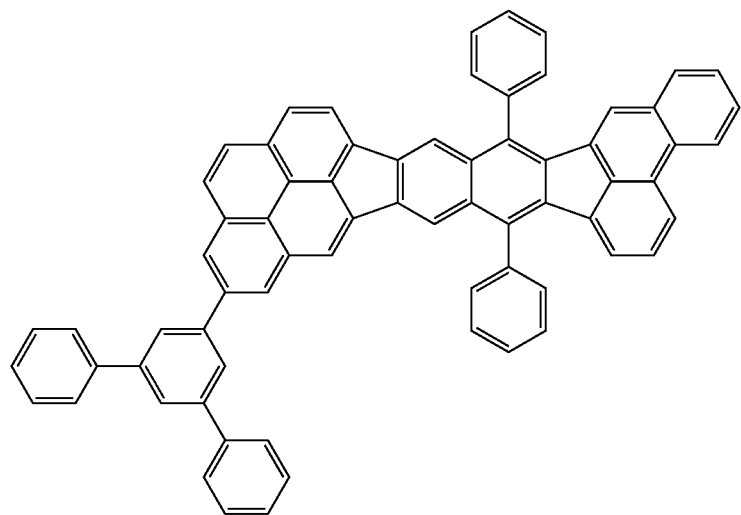
A21
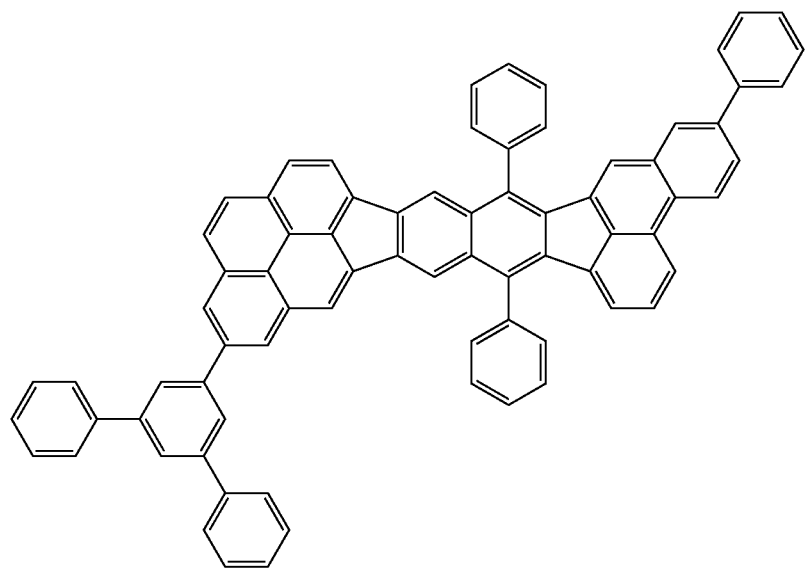
A22
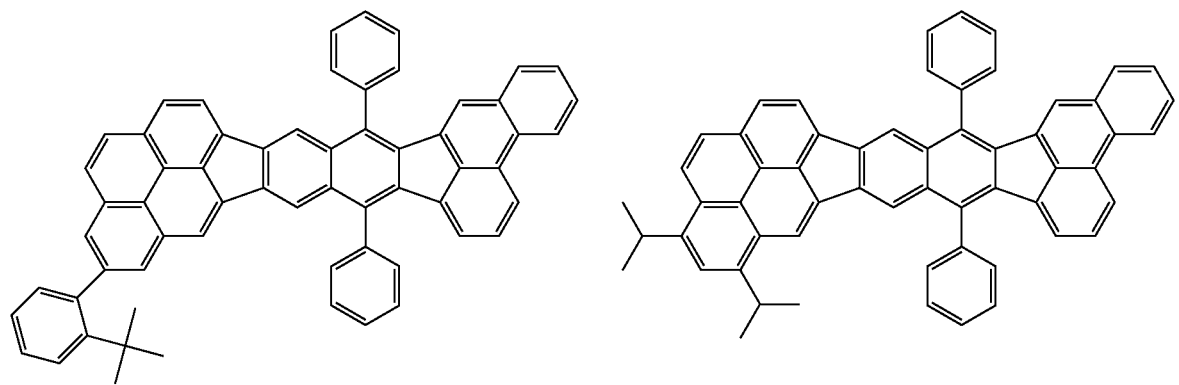
A23 A24

-continued
A25
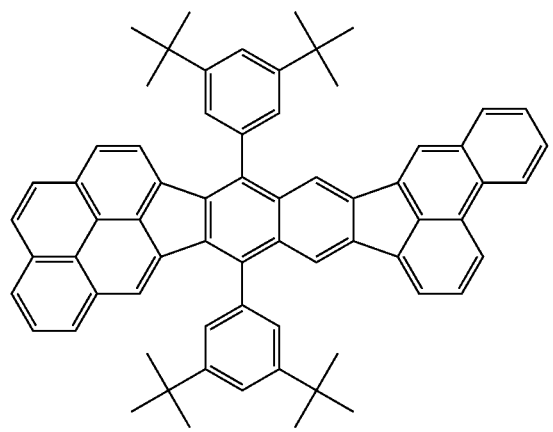
A26
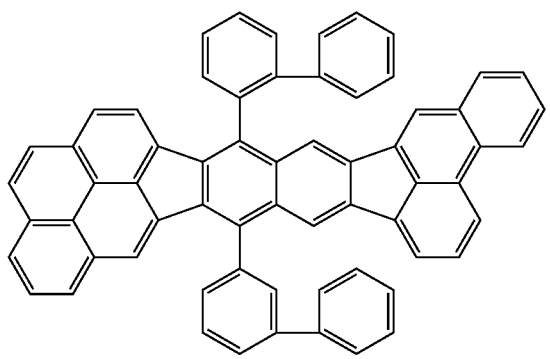
A27
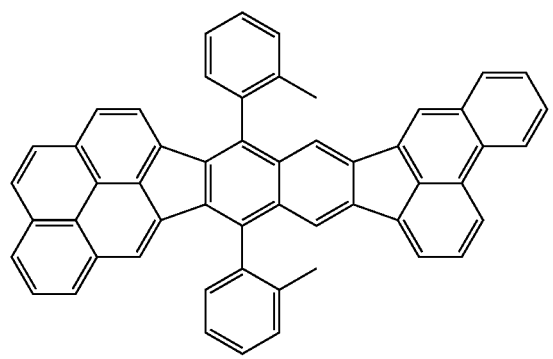
A28
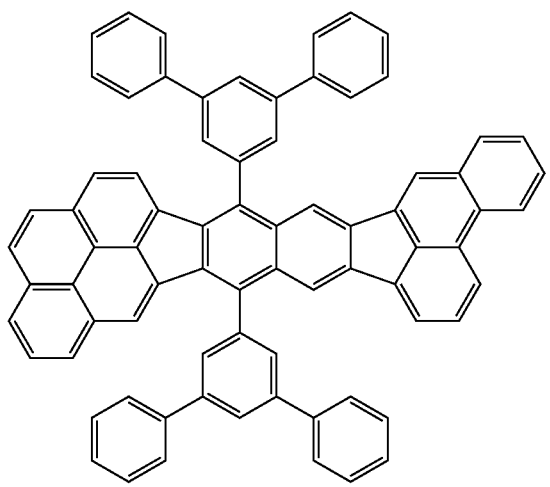
A29
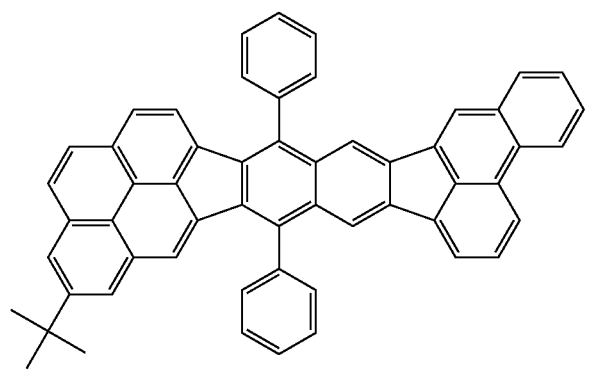
A30
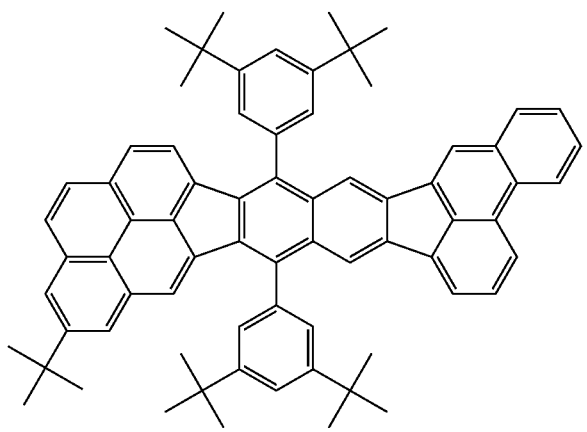

[Chem. 9]
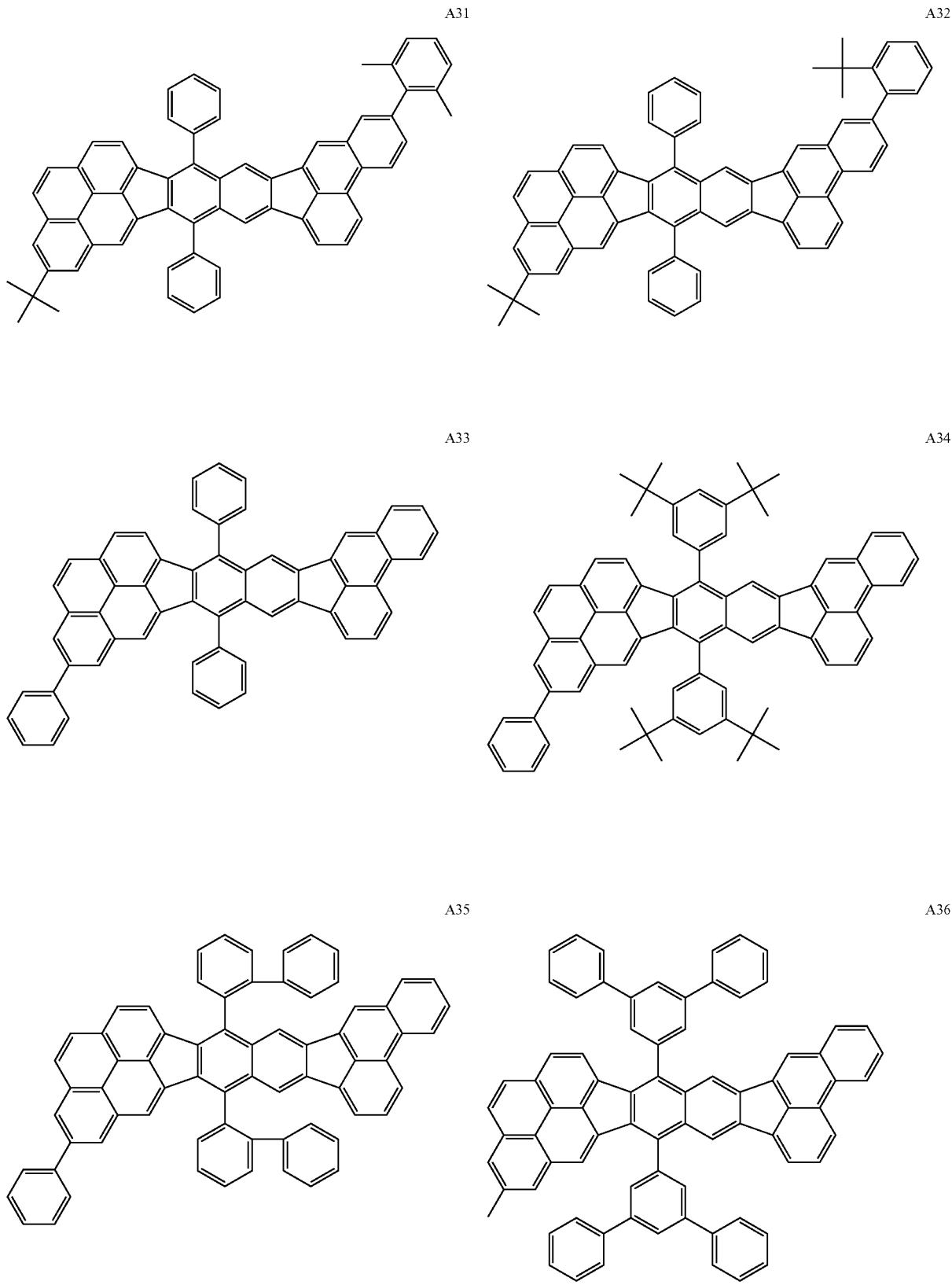

-continued
A37
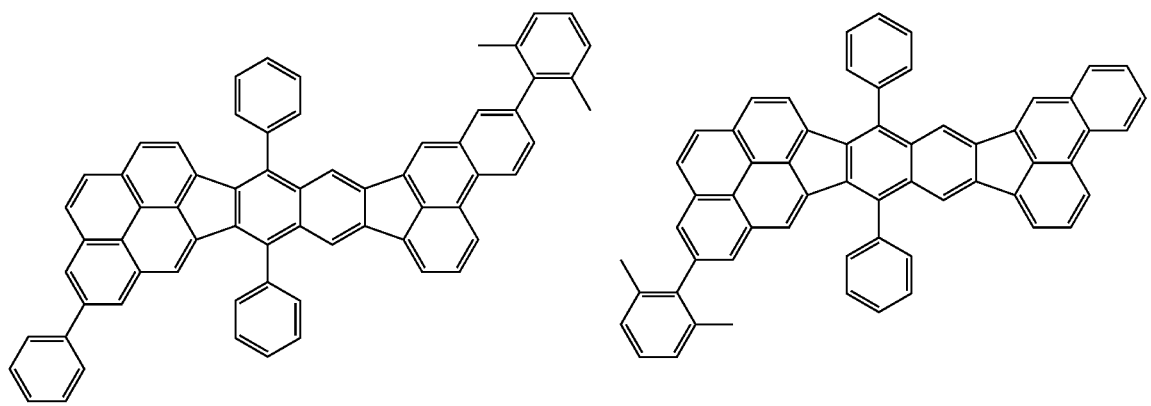
A38
A39
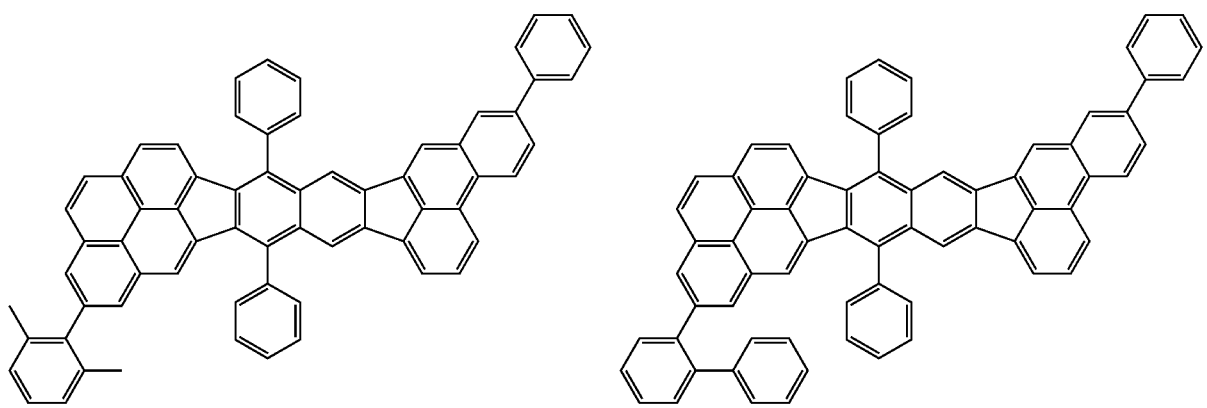
A40
A41
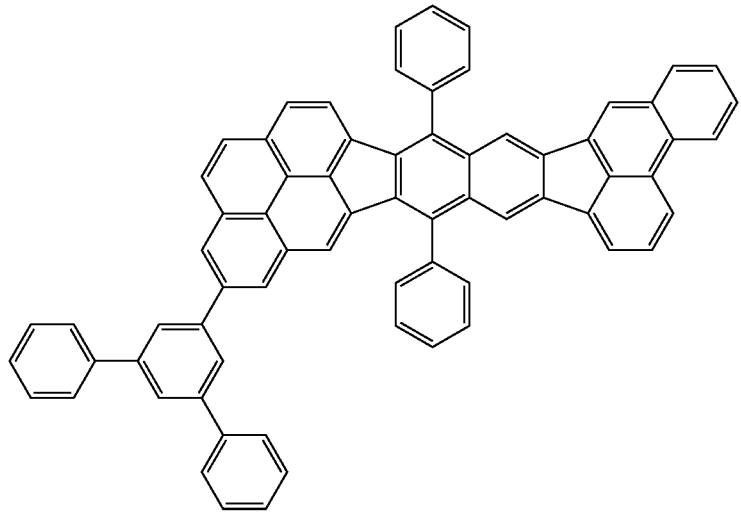

A42
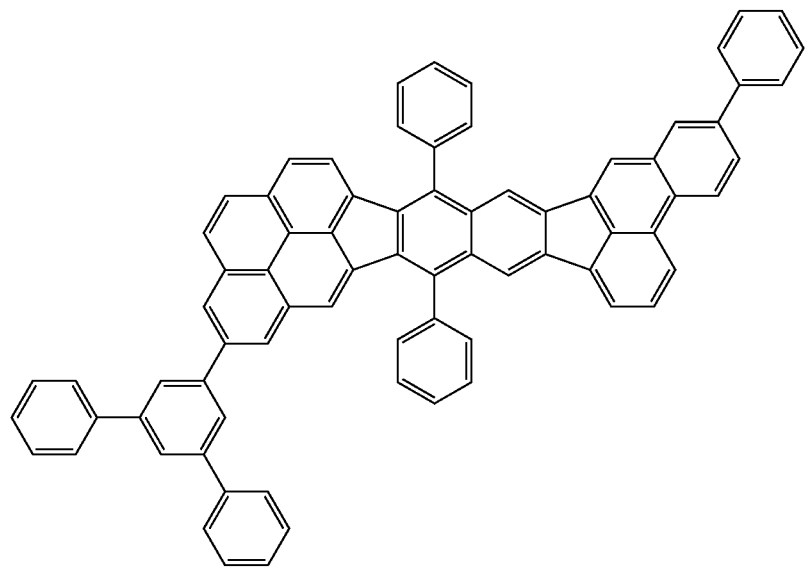
A43
A44
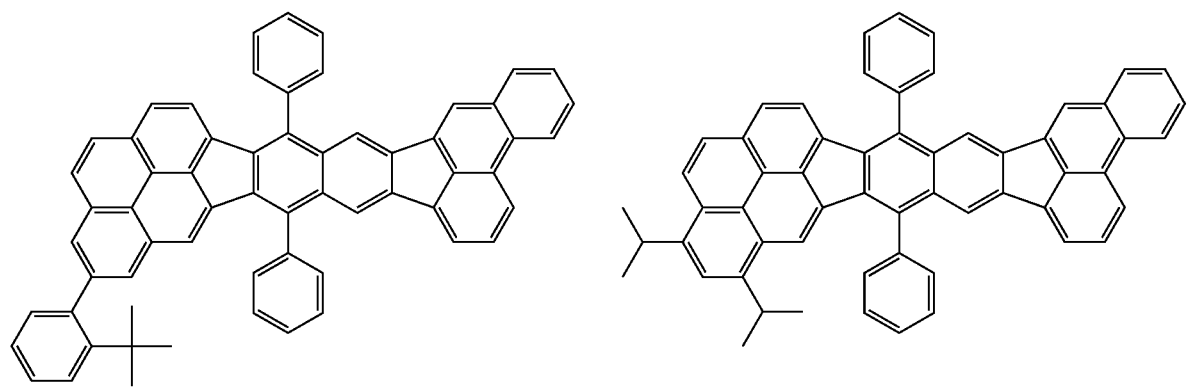
A45
A46
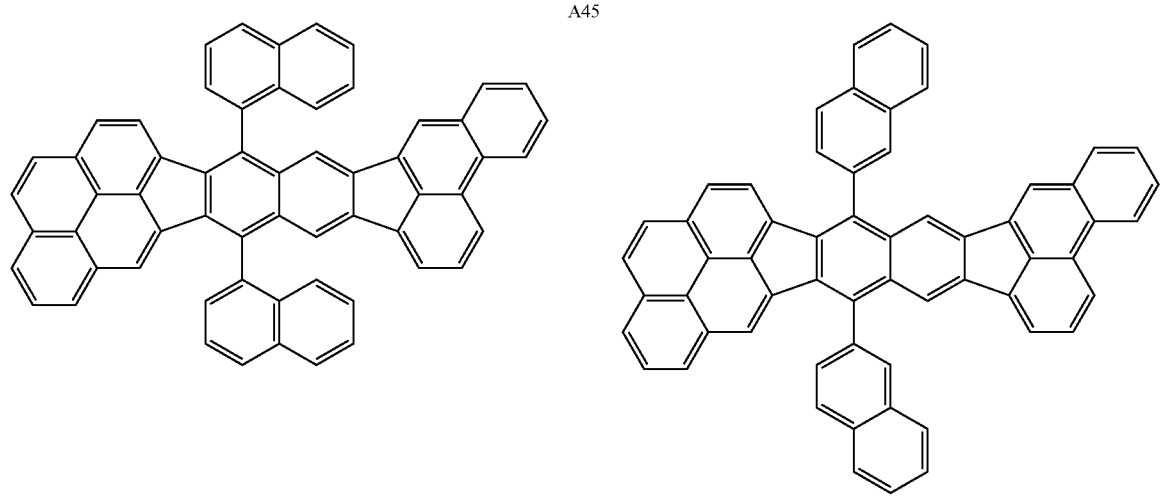

-continued
A47
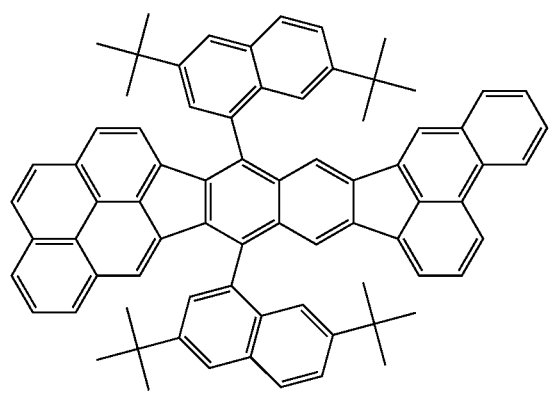
A48
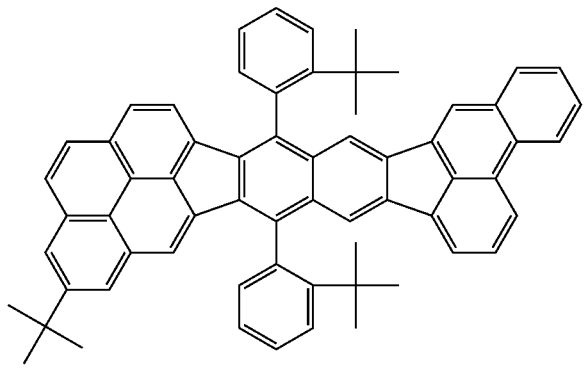
[Chem. 10]
B1
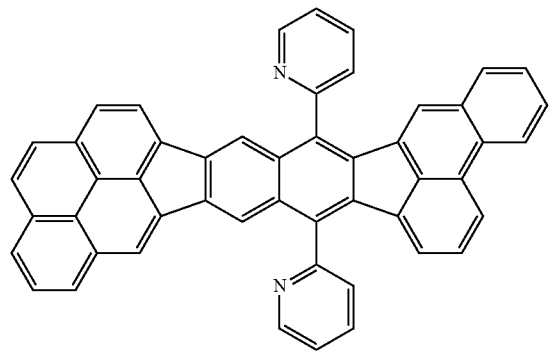
B2
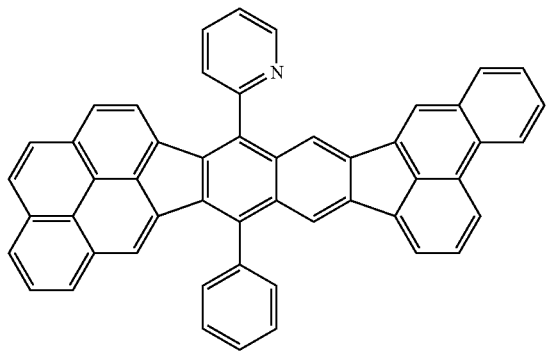
B3
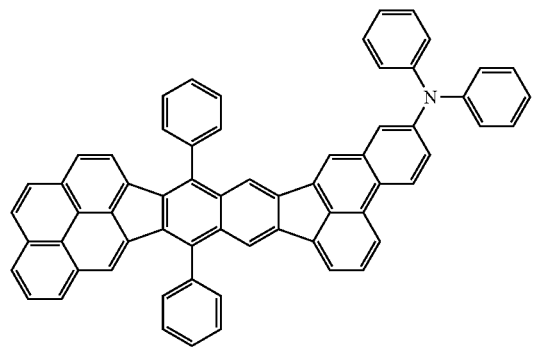
B4
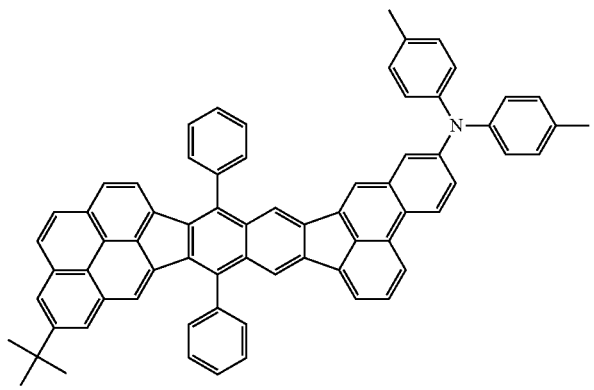
B5
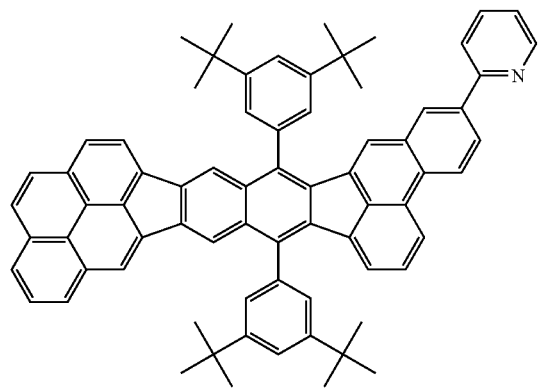
B6
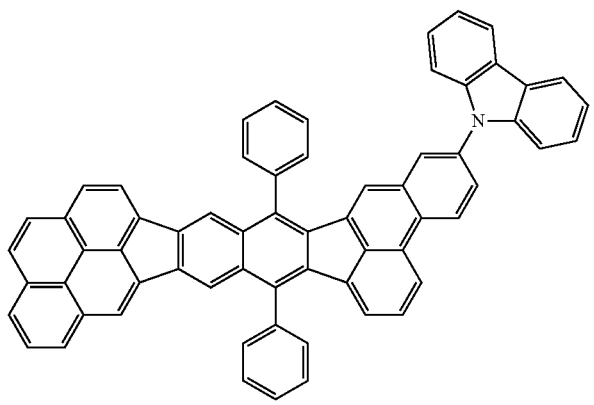

-continued

B7

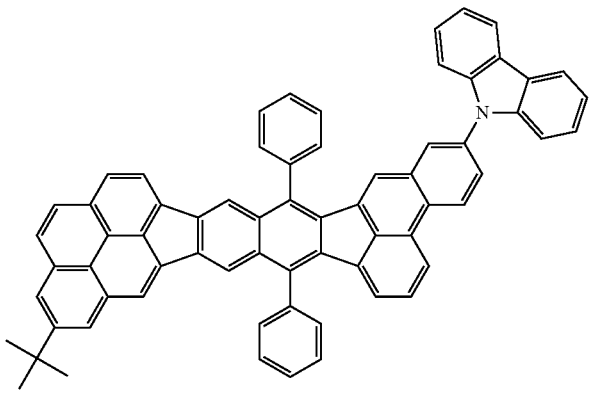

B8

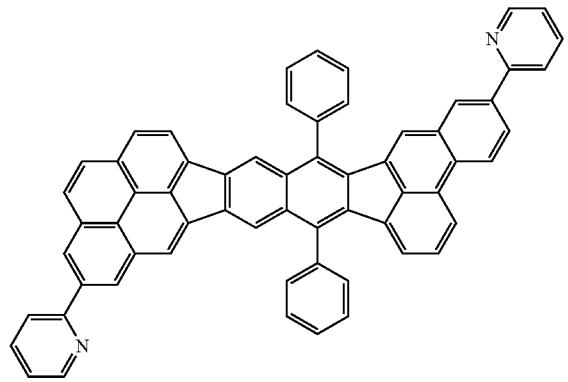

Properties of Example Compound Groups

Among example compounds shown above, the entire molecule of those of Group A is constituted by hydrocarbons only. A compound constituted by hydrocarbons only have a low HOMO energy level. This means that the oxidation potential is low and the organic compound is stable against oxidation.

Of the organic compounds of the invention, the compound of Group A constituted by hydrocarbons only, have high molecular stability and thus favored.

In formula (1), at least one aryl group is introduced into at least one position selected from $R_9$ and $R_{10}$ and at least one position selected from $R1_9$ and $R_{20}$. This is to sterically protect the nearby regions of the electron-deficient 5-membered ring moieties. Compared to other moieties formed of 6-membered ring structures, electron-deficient structures easily accept electrons and the interaction of such structures with nearby molecules may be stronger. When dimerization occurs as a result of intermolecular interaction, the energy loss is increased and the emission efficiency is lowered. It is more effective to introduce an aryl group into $R_9$, $R_{10}$, $R_{19}$, or $R_{20}$ than to introduce an aryl group to $R_1$, $R_9$, $R_{11}$, or $R_{18}$ since introduction of an aryl group into $R_9$, $R_{10}$, $R_{19}$, or $R_{20}$ has a larger effect of suppressing intermolecular interaction. This is because, due to the steric effects of the hydrogen or a substituent at a peri position, the plane of the substituent is arranged to be more perpendicular to the plane of the fused ring structure, i.e., the basic skeleton.

Accordingly, a molecular structure represented by general formula (2) is favorable.

[Chem. 11]

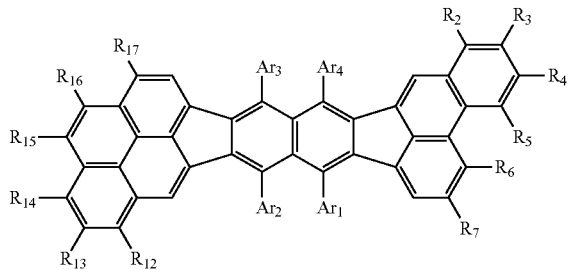

(2)

In formula (2), $Ar_1$ to $Ar_4$ are each individually selected from a hydrogen atom and an aryl group. The aryl group selected may have a substituent. At least one of $Ar_1$ and $Ar_2$ is an aryl group and at least one of $Ar_3$ and $Ar_4$ is an aryl group.

Examples of the aryl group include a phenyl group, a naphthyl group, an indenyl group, a biphenyl group, a terphenyl group, a phenanthrenyl group, a fluorenyl group, an anthracenyl group, a pyrenyl group, a fluoranthenyl group, a benzofluoranthenyl group, and a perylenyl group. A phenyl group, a biphenyl group, and a terphenyl group are preferable since they have high ability to prevent stacking and little affect the emission wavelength of the basic skeleton.

In formula (2), $R_2$ to $R_7$ and $R_{12}$ to $R_{17}$ are each individually selected from a hydrogen atom, a halogen atom, an alkyl group, an alkoxy group, an amino group, an aryl group, and a heterocyclic group. $R_2$ to $R_7$ and $R_{12}$ to $R_{17}$ may each individually be selected from a hydrogen group, an alkyl group, and an aryl group because the compound represented by formula (2) is then composed of hydrocarbons only and becomes stable against oxidation. When substituents are introduced into $R_2$ to $R_7$ and $R_{12}$ to $R_{17}$, stacking can be suppressed and the emission wavelength can be finely adjusted.

The alkyl, alkoxy, amino, aryl, and heterocyclic groups may have substituents.

When substituents contain nitrogen atoms such as the compounds of Group B, the oxidation potential of the molecule changes greatly. The intermolecular interactions may also change. When the substituents contain nitrogen atoms, the maximum emission wavelength can be made longer. When the substituents contain nitrogen atoms, the compound may be used in the electrode interface, as an electron transport material, a hole transport material, or a hole-trap-type emission material, and in a usage in which the compound is used at a 100% concentration as an emission material.

The example compounds of Groups A and B above emit green light because of the basic skeleton. The wavelength can be made longer by introducing substituents into the basic skeleton of the organic compound, e.g., the emission color may be changed from green to red. The organic compound represented by general formula (1) not limited to the example compounds may be used as a host material of the organic light-emitting device or in an electron transport layer, an electron injection layer, a hole transport layer, a hole injection layer, a hole blocking layer, or the like. In such a case, the emission color of the organic light-emitting device is not limited to green and may be red, white, or any intermediate color. The compound may also be used as an assisting material or a host material of an emission layer of a red organic light-emitting device.

Description of Synthetic Route

An example of a route for synthesizing the organic compound of an embodiment of the present invention will now be described. The reaction scheme is described below.

In the reaction scheme below, when substituents are to be introduced, hydrogen atoms at the positions where substitution are to be made are replaced with other substituents. Examples of the substituent include an alkyl group, a halogen atom, and an aryl group.

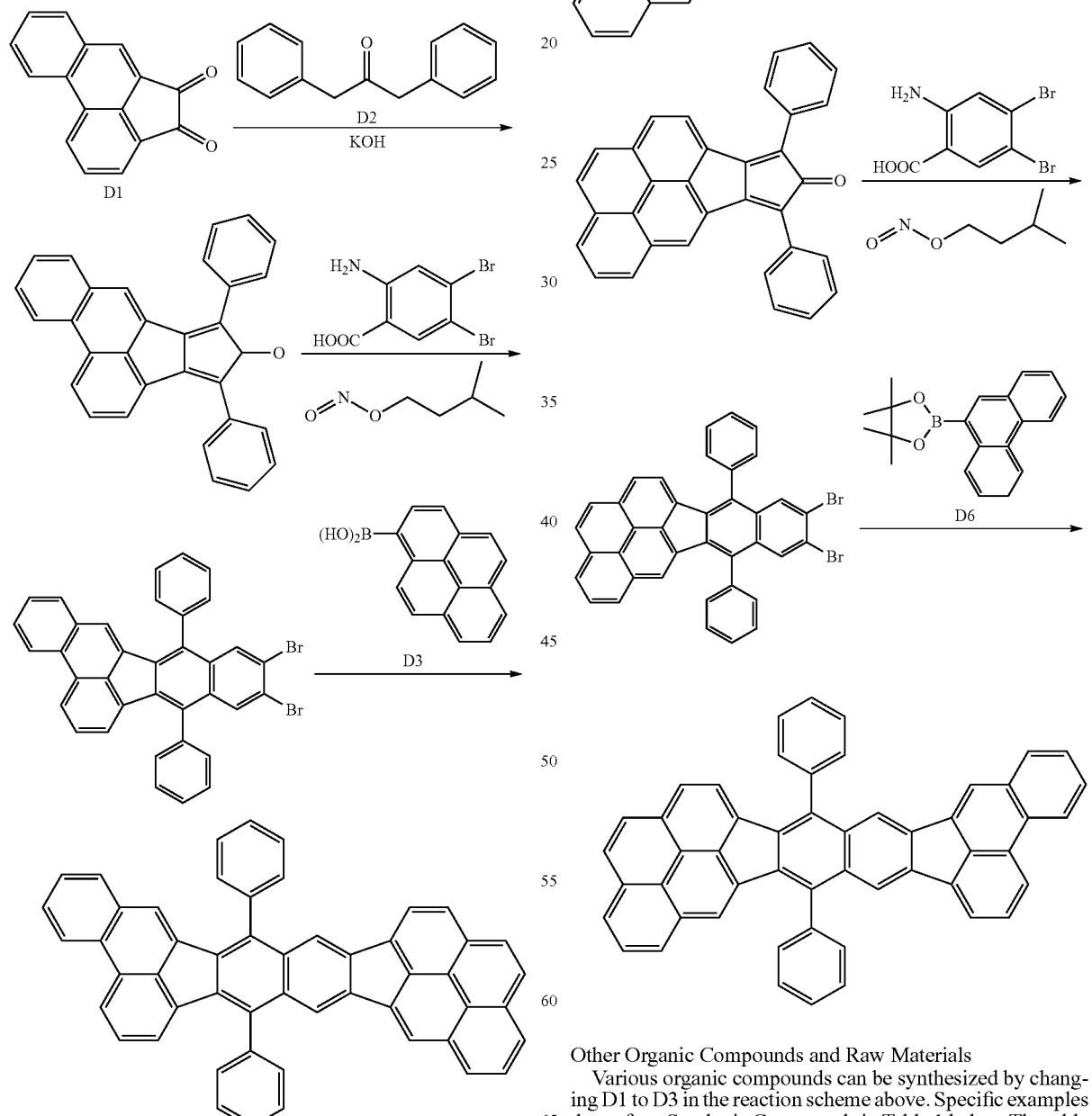

Other Organic Compounds and Raw Materials

Various organic compounds can be synthesized by changing D1 to D3 in the reaction scheme above. Specific examples thereof are Synthetic Compounds in Table 1 below. The table also shows the raw materials, i.e., D1 to D3, for preparing the synthetic compounds.

TABLE 1

| | D1 | D2 | D3 | Example Compound No. |
|---|---|---|---|---|
| Synthetic Example 1 | | | | A2 |
| Synthetic Example 2 | | | | A5 |
| Synthetic Example 3 | | | | A7 |
| Synthetic Example 4 | | | | A8 |
| Synthetic Example 5 | | | | A9 |
| Synthetic Example 6 | | | | A10 |
| Synthetic Example 7 | | | | A12 |

Various organic compounds can be synthesized by changing D4 to D6 in the reaction scheme above. Specific examples thereof are Synthetic Compounds in Table 2 below. The table also shows the raw materials, i.e., D4 to D6, for preparing the synthetic compounds.

posed between the anode and the cathode. The organic compound layer contains an organic compound represented by general formula (1).

An organic light-emitting device is a type of device in which excitons of a light-emitting organic compound in the organic compound layer are generated by carrier injection from the anode and the cathode and light is emitted as the excitons return to their ground state.

TABLE 2

| | D4 | D5 | D6 | Example Compound No. |
|---|---|---|---|---|
| Synthetic Example 8 |  | 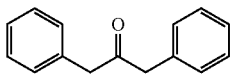 | 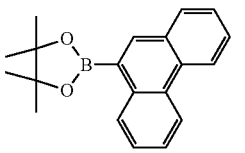 | A3 |
| Synthetic Example 9 | 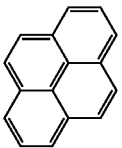 | 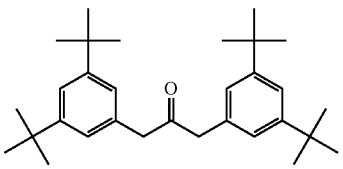 | 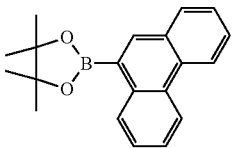 | A25 |
| Synthetic Example 10 | 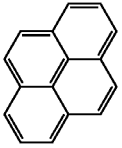 | 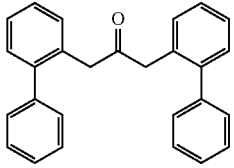 | 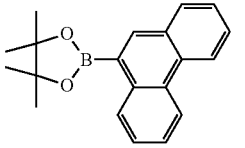 | A26 |
| Synthetic Example 11 |  | 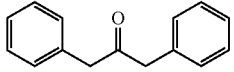 | 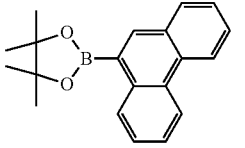 | A29 |
| Synthetic Example 12 | 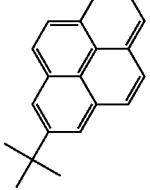 | 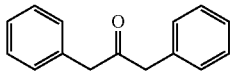 | 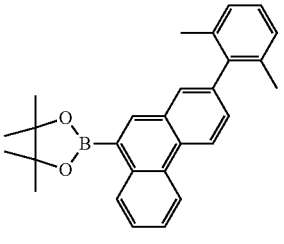 | A31 |
| Synthetic Example 13 | 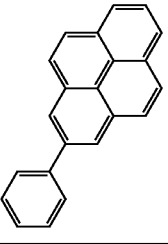 | 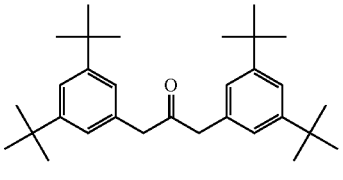 | 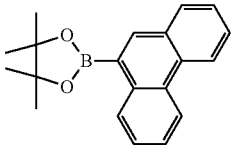 | A34 |

Description of Organic Light-Emitting Device

An organic light-emitting device according to an embodiment of the invention will now be described.

An organic light-emitting device according to an embodiment of the invention includes a pair of electrodes, i.e., an anode and a cathode, and an organic compound layer interposed between the anode and the cathode. The organic compound layer contains an organic compound represented by general formula (1).

When the organic compound layer is an emission layer, the emission layer may be solely composed of the organic compound of the embodiment or may contain other components.

When the emission layer contains the organic compound of the embodiment and other components, the organic compound of the embodiment may be a main component or an auxiliary component of the emission layer.

A main component is a component having the largest weight ratio among the compounds constituting the emission layer. An auxiliary component is a component having a weight ratio smaller than that of the main component among the compounds constituting the emission layer.

The material contained as a main component may be referred to as a "host material".

The material contained as an auxiliary component is a dopant (guest) material. Other examples of the auxiliary component include an emission assist material and a charge injection material.

When the organic compound of the embodiment is used as a guest material, the concentration of the guest material relative to the host material is preferably 0.01 to 20 wt % and more preferably 0.5 to 10 wt %.

The inventors have conductive a variety of investigations and have found that a device that uses the organic compound represented by general formula (1) as a host or guest material of an emission layer, in particular, a guest material of an emission layer, offers optical output at high efficiency and high luminance and has significantly high durability.

Examples of the organic light-emitting device that uses the organic compound of the embodiment are as follows.

Examples of the structure of the organic light-emitting device include a structure in which an anode, an emission layer, and a cathode are sequentially formed on a substrate, a structure in which an anode, a hole transport layer, an electron transport layer, and a cathode are sequentially formed on a substrate, a structure in which an anode, a hole transport layer, an emission layer, an electron transport layer, and a cathode are sequentially formed on a substrate, a structure in which an anode, a hole injection layer, a hole transport layer, an emission layer, an electron transport layer, and a cathode are sequentially formed on a substrate, and a structure in which an anode, a hole transport layer, an emission layer, a hole/exciton blocking layer, an electron transport layer, and a cathode are sequentially formed on a substrate. However, these five types of multilayer structures are merely basic configurations of the devices, and the structure of the organic light-emitting device that uses the compound of the embodiment is not limited to these. Various other layer configurations may be employed, e.g., an insulating layer may be provided at the interface between an electrode and an organic compound layer, an adhesive layer or an interference layer may be provided, and the electron transport layer or the hole transport layer may be constituted by two layers having different ionization potentials.

The organic compound represented by general formula (1) can be used in an organic compound layer of a light-emitting device having any one of the aforementioned layer configurations.

If needed, a hole injection compound, a hole injection compound, a hole transport compound, a host compound that can be used as a host material, a light-emitting compound, an electron injection compound, an electron transport compound, etc., that are widely used may be used in combination with the organic compound of the embodiment. Such compounds may be low-molecular compounds or high-molecular compounds.

Specific examples of such compounds are as follows.

The hole injection compound and the hole transport compound may be material having a high hole mobility. Examples of the low-molecular and high-molecular compounds having hole injection property or hole transport property include, but are not limited to, triarylamine derivatives, phenylenediamine derivatives, stilbene derivatives, phthalocyanine derivative, porphyrin derivatives, poly(vinylcarbazole), poly(thiophene), and other conductive polymers.

Examples of the structural formulae of the host compound are shown in Table 3. The host compound may be a derivative of a compound represented by any of the structural formulae in Table 3. Other examples of the host compound include, but are not limited to, fused ring compounds (e.g., fluorene derivatives, naphthalene derivatives, anthracene derivative, pyrene derivatives, carbazole derivatives, quinoxaline derivative, and quinoline derivatives), organic aluminum complexes such as tris(8-quinolinolato)aluminum, organic zinc complexes, triphenyl amine derivatives, and polymer derivatives such as poly(fluorene) derivatives and poly(phenylene) derivatives.

TABLE 3

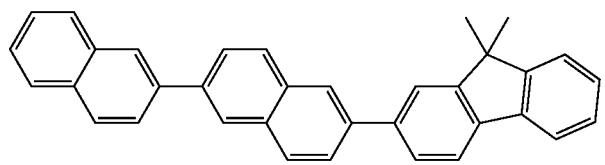 [SMILES: CC1(C)c2ccccc2-c2ccc(-c3ccc4cc(-c5ccc6ccccc6c5)ccc4c3)cc21]

H1

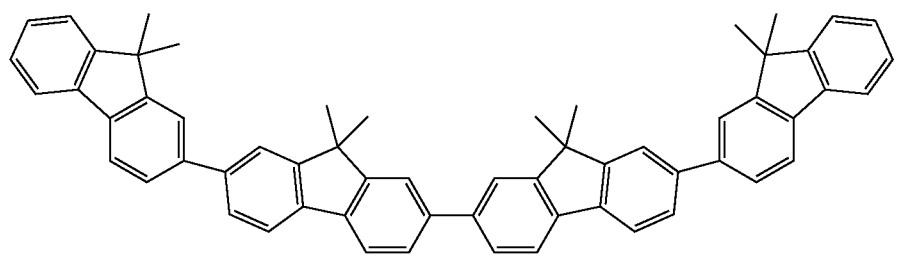 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]

H2

TABLE 3-continued
H3
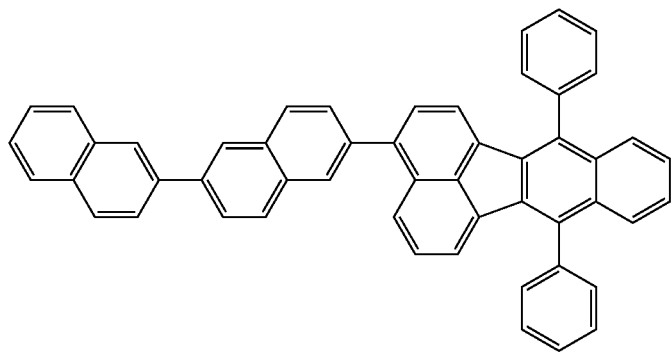 [SMILES: c1ccc(-c2c3c(c(-c4ccccc4)c4ccccc24)-c2ccc(-c4ccc5cc(-c6ccc7ccccc7c6)ccc5c4)c4cccc-3c24)cc1]
H4
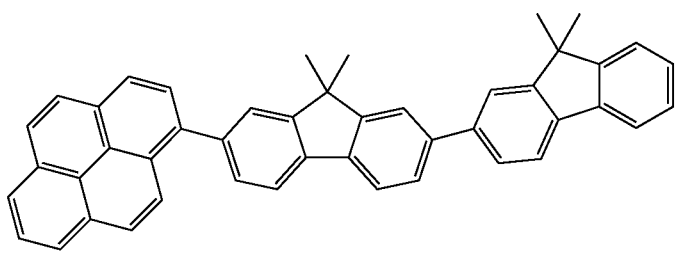 [SMILES: CC1(C)c2ccccc2-c2ccc(-c3ccc4c(c3)C(C)(C)c3cc(-c5ccc6ccc7cccc8ccc5c6c78)ccc3-4)cc21]
H5
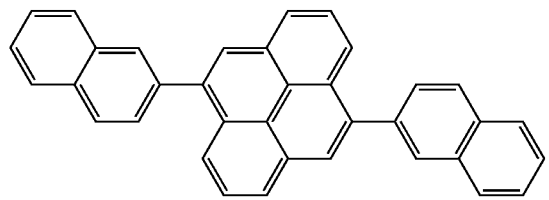 [SMILES: c1ccc2cc(-c3cc4cccc5c(-c6ccc7ccccc7c6)cc6cccc3c6c45)ccc2c1]
H6
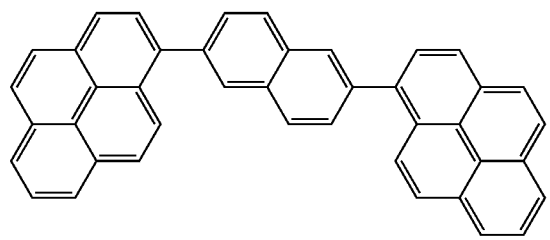 [SMILES: c1cc2ccc3ccc(-c4ccc5cc(-c6ccc7ccc8cccc9ccc6c7c89)ccc5c4)c4ccc(c1)c2c34]
H7
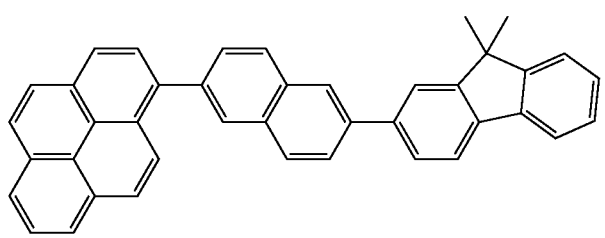 [SMILES: CC1(C)c2ccccc2-c2ccc(-c3ccc4cc(-c5ccc6ccc7cccc8ccc5c6c78)ccc4c3)cc21]

TABLE 3-continued
H8
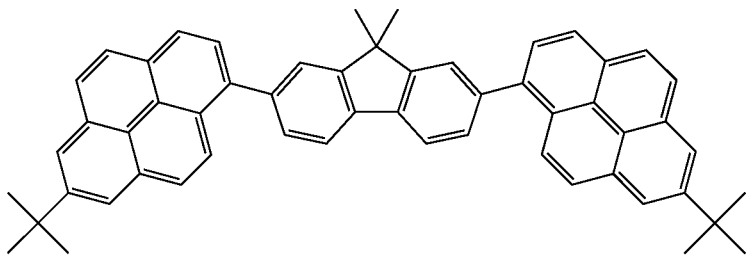 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H9
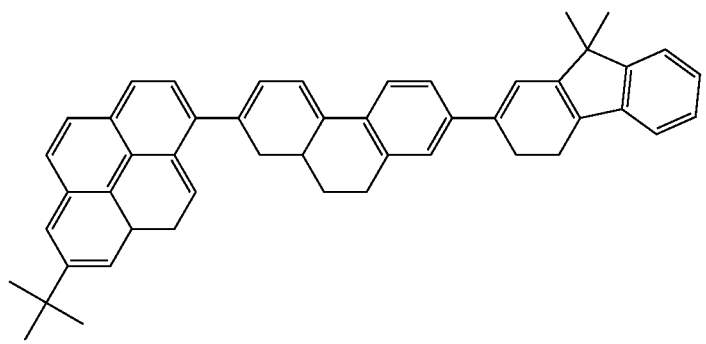 [SMILES: CC(C)(C)C1=CC2CC=c3c(C4=CC=C5c6ccc(C7=CC8=C(CC7)c7ccccc7C8(C)C)cc6CCC5C4)ccc4ccc(c2c34)=C1]
H10
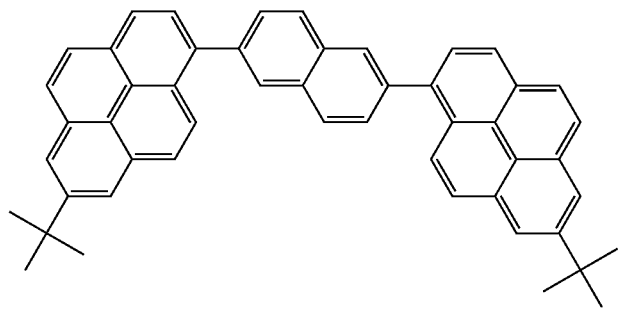 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
H11
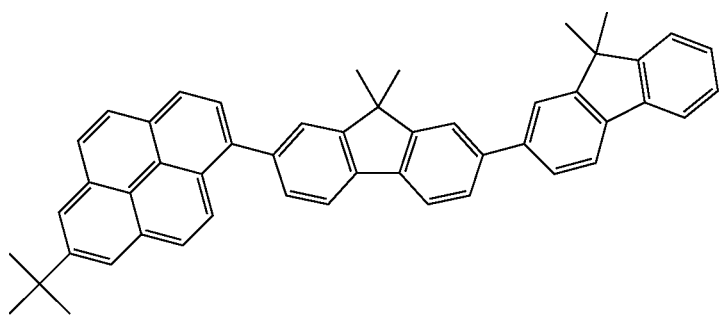 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]

TABLE 3-continued
H12
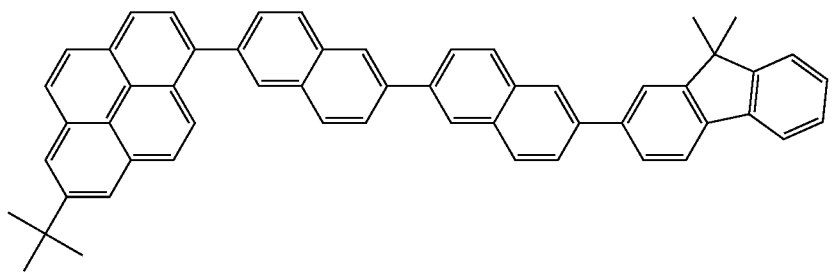 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34]
H13
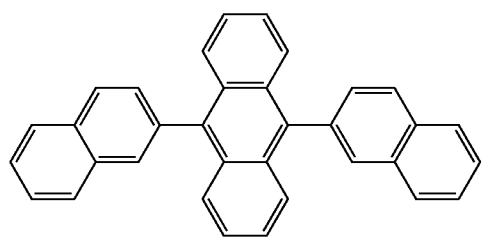 [SMILES: c1ccc2cc(-c3c4ccccc4c(-c4ccc5ccccc5c4)c4ccccc34)ccc2c1]
H14
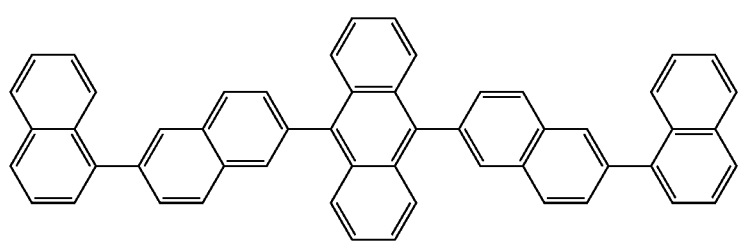 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H15
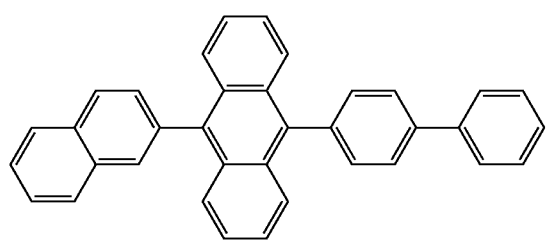 [SMILES: c1ccc(-c2ccc(-c3c4ccccc4c(-c4ccc5ccccc5c4)c4ccccc34)cc2)cc1]
H16
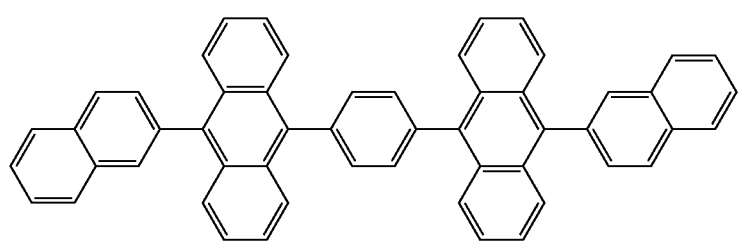 [SMILES: c1ccc2cc(-c3c4ccccc4c(-c4ccc(-c5c6ccccc6c(-c6ccc7ccccc7c6)c6ccccc56)cc4)c4ccccc34)ccc2c1]

TABLE 3-continued
H17
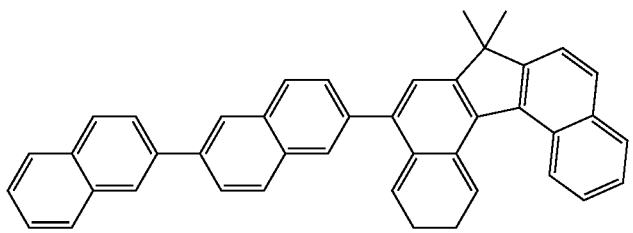 [SMILES: CC1(C)c2cc(-c3ccc4cc(-c5ccc6ccccc6c5)ccc4c3)c3c(c2-c2c1ccc1ccccc21)=CCCC=3]
H18
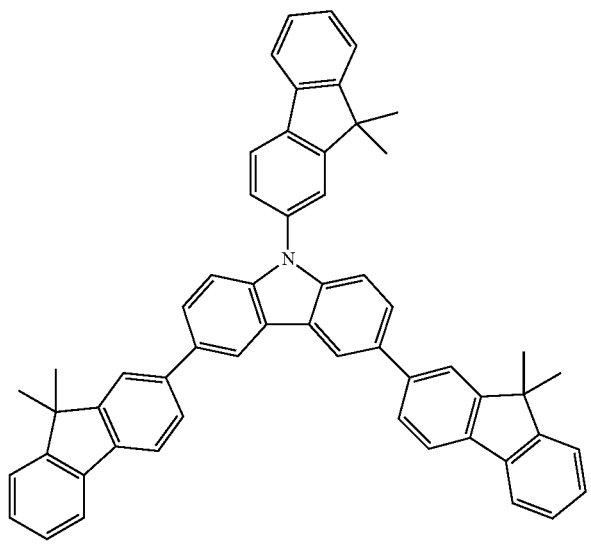 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H19
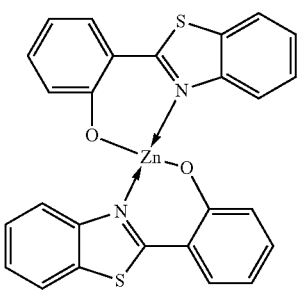
H20
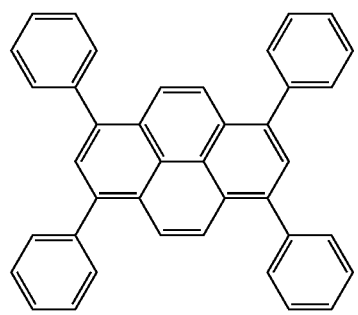 [SMILES: c1ccc(-c2cc(-c3ccccc3)c3ccc4c(-c5ccccc5)cc(-c5ccccc5)c5ccc2c3c54)cc1]

TABLE 3-continued
H21
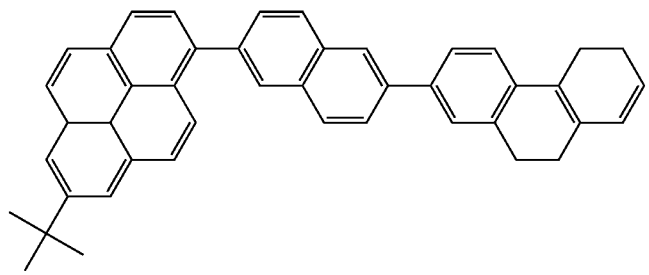 [SMILES: CC(C)(C)C1=CC2C=Cc3ccc(-c4ccc5cc(-c6ccc7c(c6)CCC6=C7CCC=C6)ccc5c4)c4c3C2C(=C1)C=C4]
H22
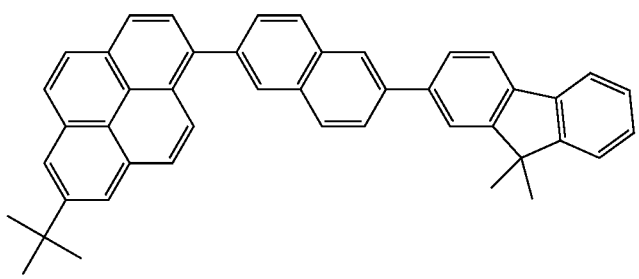 [SMILES: CC(C)(C)c1cc2ccc3ccc(-c4ccc5cc(-c6ccc7c(c6)C(C)(C)c6ccccc6-7)ccc5c4)c4ccc(c1)c2c34]
H23
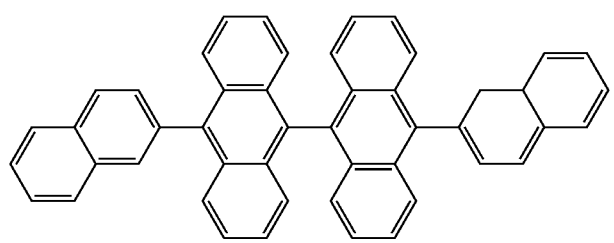 [SMILES: C1=CC2=CC=C(c3c4ccccc4c(-c4c5ccccc5c(-c5ccc6ccccc6c5)c5ccccc45)c4ccccc34)CC2C=C1]
H24
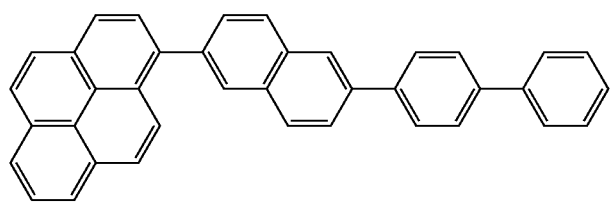 [SMILES: c1ccc(-c2ccc(-c3ccc4cc(-c5ccc6ccc7cccc8ccc5c6c78)ccc4c3)cc2)cc1]
H25
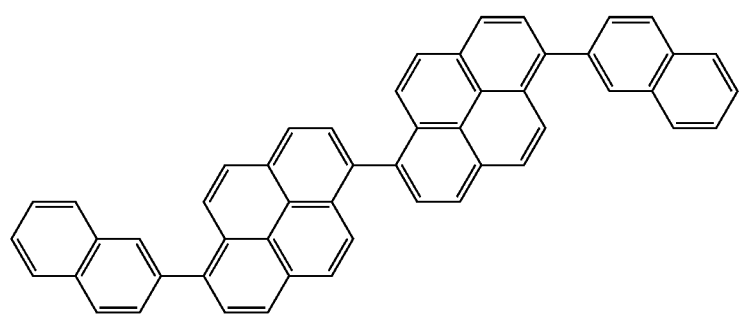 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1]

TABLE 3-continued

H26
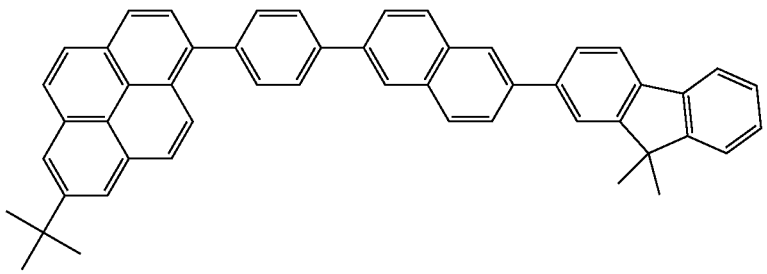 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34]

H27
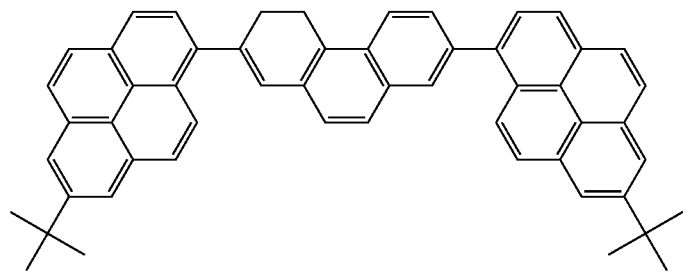 [SMILES: CC(C)(C)c1cc2ccc3ccc(C4=Cc5ccc6cc(-c7ccc8ccc9cc(C(C)(C)C)cc%10ccc7c8c9%10)ccc6c5CC4)c4ccc(c1)c2c34]

H28
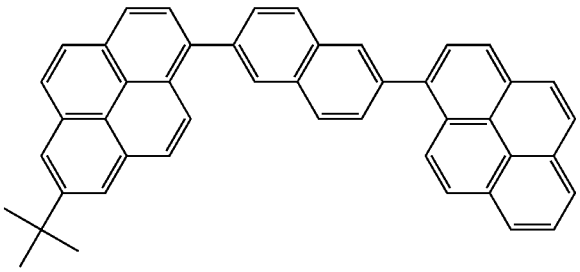 [SMILES: CC(C)(C)c1cc2ccc3ccc(-c4ccc5cc(-c6ccc7ccc8cccc9ccc6c7c89)ccc5c4)c4ccc(c1)c2c34]

The selection of the electron injection compound or the electron transport compound is made by considering balance with the hole mobility of the hole injection compound or the hole transport compound. Examples of the compound having the electron injection property or the electron transport property include, but are not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

The anode material may have a large work function. Examples of the anode material include single metals such as gold, platinum, silver, copper, nickel, palladium, cobalt, selenium, vanadium, and tungsten or alloys thereof, and metal oxides such as tin oxide, zinc oxide, indium oxide, indium tin oxide (ITO), and indium zinc oxide. Conductive polymers such as polyaniline, polypyrrole, and polythiophene may also be used. These anode materials may be used alone or in combination. The anode may be constituted by one layer or two or more layers.

The cathode material may have a small work function. Examples of the cathode material include alkali metals such as lithium, alkaline earth metals such as calcium, and single metals such as aluminum, titanium, manganese, silver, lead, and chromium. The single metals may be combined and used as alloys. For example, magnesium-silver, aluminum-lithium, and aluminum-magnesium alloys and the like can be used. Metal oxides such as indium tin oxide (ITO) can also be used. These cathode materials may be used alone or in combination. The cathode may be constituted by one layer or two or more layers.

A layer containing the organic compound of the embodiment and a layer composed of other organic compound of the organic light-emitting device of the embodiment are prepared by the methods below. Typically, thin films are formed by vacuum vapor deposition, ionization deposition, sputtering, plasma, and coating using an adequate solvent (spin-coating, dipping, casting, a Langmuir Blodgett method, and an ink jet method). When layers are formed by vacuum vapor deposition or a solution coating method, crystallization is suppressed and stability over time can be improved. When a coating method is employed, an adequate binder resin may be additionally used to form a film.

Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins. These binder resins may be used alone as a homopolymer or in combination of two or more as a copolymer. If needed, known additives such as a plasticizer, an antioxidant, and an ultraviolet absorber may be used in combination.

Usage of Organic Light-Emitting Device

The organic light-emitting device of the embodiment may be used in a display apparatus or a lighting apparatus. The organic light-emitting device can also be used as exposure light sources of image-forming apparatuses and backlights of liquid crystal display apparatuses.

A display apparatus includes a display unit that includes the organic light-emitting device of this embodiment. The display unit has pixels and each pixel includes the organic light-emitting device of this embodiment. The display apparatus may be used as an image display apparatus of a personal computer, etc.

The display apparatus may be used in a display unit of an imaging apparatus such as digital cameras and digital video cameras. An imaging apparatus includes the display unit and an imaging unit having an imaging optical system for capturing images.

Next, a display apparatus that includes the organic light-emitting device of the embodiment is described.

FIG. 1 is a schematic cross-sectional view of a substrate that includes an organic light-emitting device of an embodiment and a thin film transistor (TFT) which is a switching element for driving the organic light-emitting device. The details of the structure are described below.

As shown in FIG. 1, a display apparatus 3 includes a TFT 38, a contact hole (through hole) 310, an anode 311, an organic layer 312, and a cathode 313. A moisture proof film 32 for protecting the TFT 38 or the organic layer 312 is formed on a substrate 31 composed of glass of the like. The display apparatus also includes a metal gate electrode 33 composed of chromium or the like, a gate insulating film 34, and a semiconductor layer 35.

The TFT 38 includes the semiconductor layer 35, a drain electrode 36, and a source electrode 37. An insulating film 39 is formed on the TFT 38. The anode 311 of the organic light-emitting device is connected to the source electrode 37 through the contact hole (through hole) 310.

The organic layer 312 in the drawing is depicted as a single layer although it has a multilayer structure. A first protective layer 314 and a second protective layer 315 for suppressing deterioration of the organic light-emitting device are provided over the cathode 313.

The luminance of the organic light-emitting device is controlled by the TFT. Plural organic light-emitting devices may be disposed on a surface and an image may be displayed by controlling the luminance of the devices.

When a display apparatus using the organic light-emitting device of the embodiment is driven, high-quality images can be displayed stably for a prolonged time.

EXAMPLES

Examples will now be described. Note that the present invention is not limited to these examples.

Example 1

Synthesis of Example Compound A2

[Chem. 14]

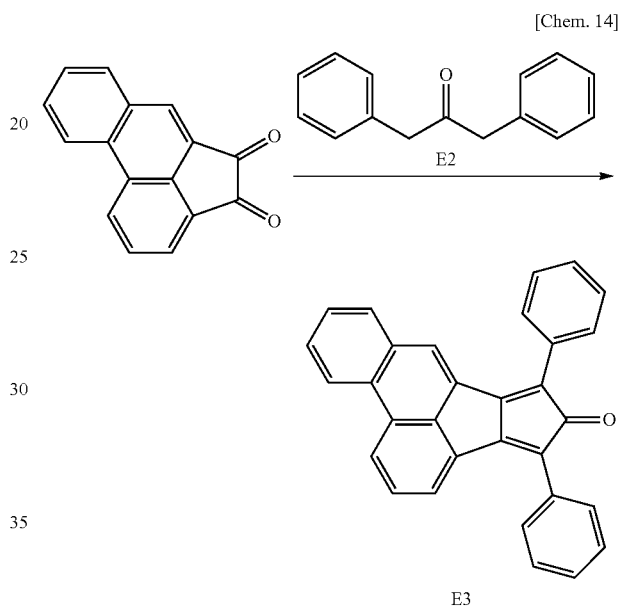

To 100 ml of ethanol, 5.8 g (25 mmol) of E1 and 5.3 g (25 mmol) of E2 were added. The mixture was heated to 60° C., and 10 ml of a 5M aqueous sodium hydroxide solution was added thereto dropwise. Upon completion of dropwise addition, the mixture was heated to 80° C., stirred for 2 hours, cooled, and filtered to recover precipitates. The precipitates were washed with water and ethanol, dried at 80° C. under heating at a reduced pressure. As a result, 8.1 g (yield: 80%) of dark green solid E3 was obtained.

[Chem. 15]

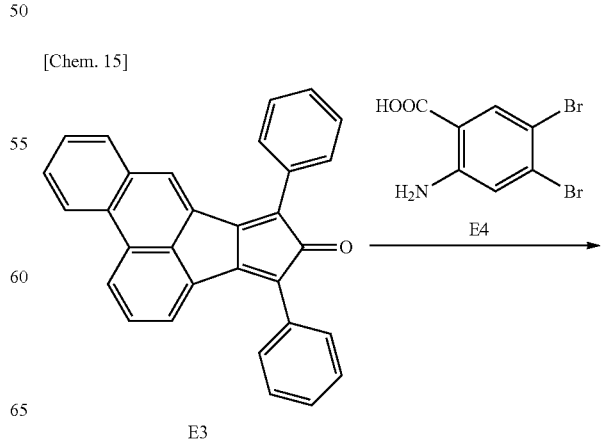

-continued

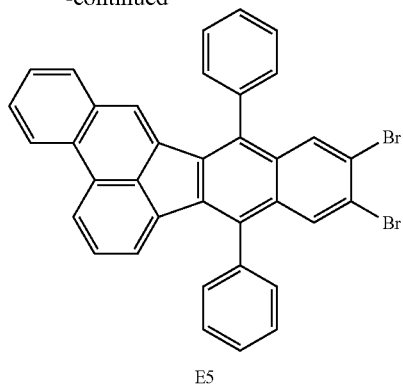

E5

To 80 ml of toluene, 3.0 g (7.3 mmol) of E3 and 3.2 g (8.0 mmol) of E4 were added. The mixture was heated to 80° C., and 0.94 g (8.0 mmol) of isoamyl nitrite was gradually added dropwise and stirred for 3 hours at 110° C. After cooling, the mixture was washed twice with 100 ml of water each time. The organic layer was washed with saturated saline and dried with magnesium sulfate. The resulting solution was filtered and the filtrate was condensed to obtain a dark brown liquid. The liquid was purified by column chromatography (toluene:heptane=1:1) and recrystallized with chloroform and ethanol. As a result, 3.2 g (yield: 72%) of yellow crystals E5 were obtained.

[Chem. 16]

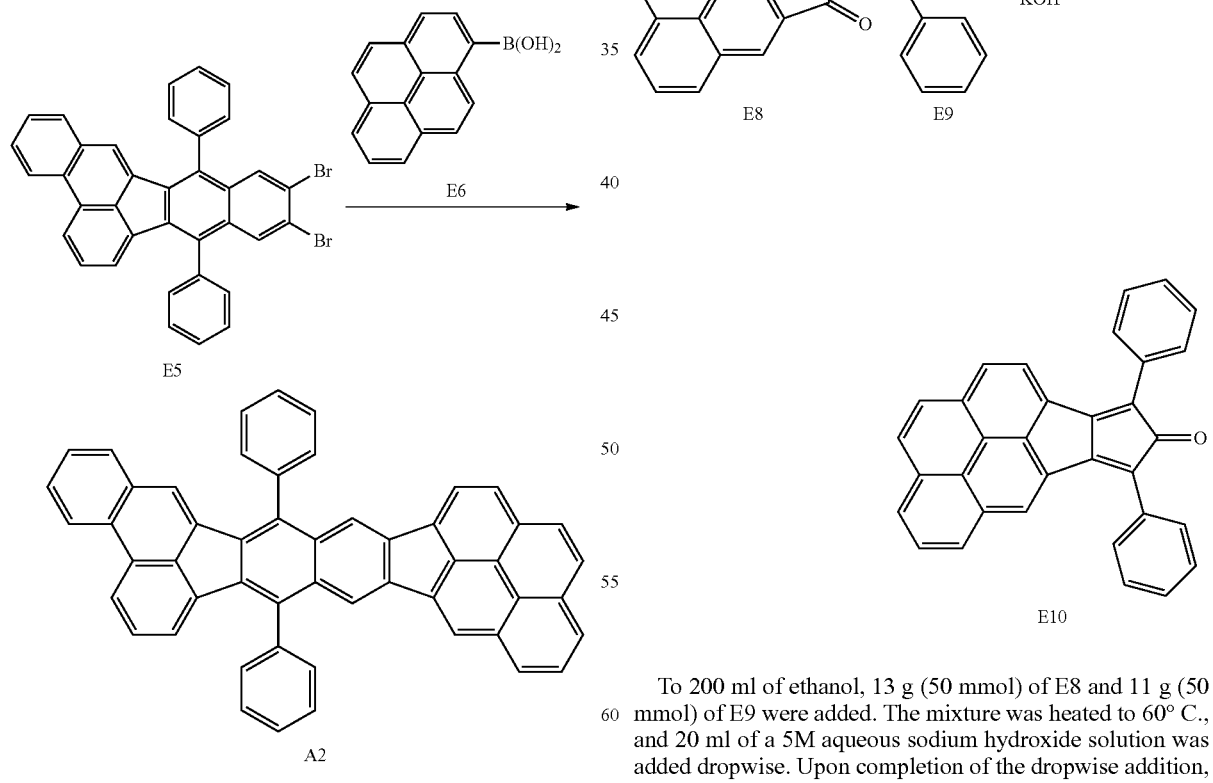

Next, 2.2 g (3.6 mmol) of E5, 1.8 g (7.2 mmol) of 1-pyreneboronic acid, 660 mg (0.72 mmol) of tris(dibenzylideneacetone)dipalladium(0), 800 mg (2.9 mmol) of tricyclohexylphosphine, 5.4 ml of diazabicycloundecene, and 36 ml of dimethylformamide were heated to reflux, and the mixture was stirred for 6 hours. After cooling, 20 ml of methanol was added thereto, and deposits were filtered. The obtained powder was dissolved in 50 ml of chloroform and washed twice with 100 ml of water each time. The organic layer was washed with saturated saline and dried with magnesium sulfate. The resulting solution was filtered and the filtrate was condensed to obtain a yellow liquid. The yellow liquid was purified by column chromatography (toluene:heptane=1:4) and recrystallized with chloroform and methanol. As a result, 1.1 g (yield: 51%) of yellow crystals A2 were obtained.

The emission spectrum of a $1\times10^{-5}$ mol/L toluene solution of Example Compound A2 was taken with F-4500 produced by Hitachi Corporation at an excitation wavelength of 350 nm by measuring the photoluminescence. A spectrum having the maximum intensity at 485 nm was obtained as a result.

Example 2

Synthesis of Example Compound A3

[Chem. 17]

To 200 ml of ethanol, 13 g (50 mmol) of E8 and 11 g (50 mmol) of E9 were added. The mixture was heated to 60° C., and 20 ml of a 5M aqueous sodium hydroxide solution was added dropwise. Upon completion of the dropwise addition, the mixture was heated to 80° C., stirred for 2 hours, cooled, and filtered to recover precipitates. The precipitates were washed with water and ethanol and dried at 80° C. under heating at a reduced pressure. As a result, 18 g (yield: 85%) of dark green solid E6 was obtained.

[Chem. 18]

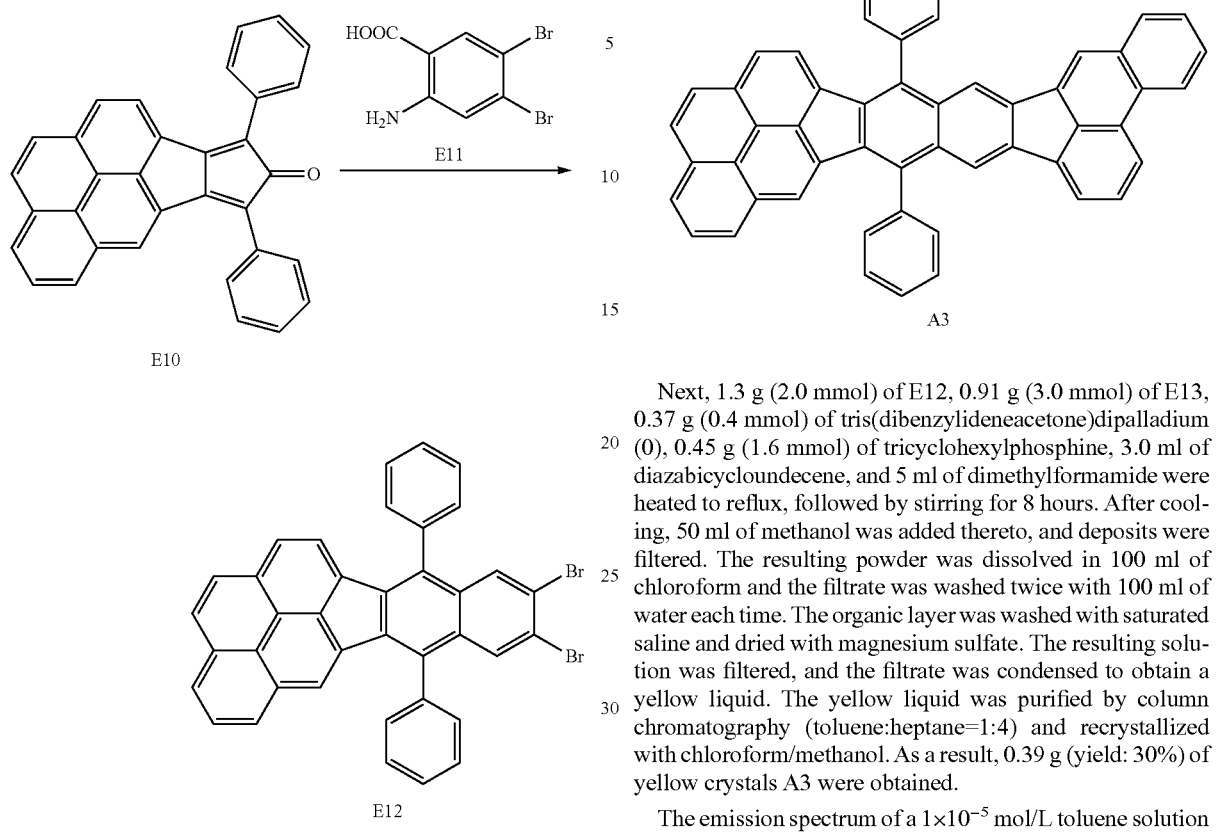

To 100 ml of toluene, 4.3 g (10 mmol) of E10 and 3.2 g (11 mmol) of E11 were added. The mixture was heated to 80° C., and 1.3 g (11 mmol) of isoamyl nitrite was gradually added thereto dropwise, followed by stirring for 5 hours at 110° C. After cooling, the mixture was washed twice with 100 ml of water each time. The organic layer was washed with saturated saline and dried with magnesium sulfate. The resulting solution was filtered and the filtrate was condensed to obtain a brown liquid. The brown liquid was purified by column chromatography (toluene:heptane=1:1) and recrystallized with chloroform and ethanol. As a result, 5.4 g (yield: 85%) of yellow crystals E12 were obtained.

[Chem. 19]

Next, 1.3 g (2.0 mmol) of E12, 0.91 g (3.0 mmol) of E13, 0.37 g (0.4 mmol) of tris(dibenzylideneacetone)dipalladium (0), 0.45 g (1.6 mmol) of tricyclohexylphosphine, 3.0 ml of diazabicycloundecene, and 5 ml of dimethylformamide were heated to reflux, followed by stirring for 8 hours. After cooling, 50 ml of methanol was added thereto, and deposits were filtered. The resulting powder was dissolved in 100 ml of chloroform and the filtrate was washed twice with 100 ml of water each time. The organic layer was washed with saturated saline and dried with magnesium sulfate. The resulting solution was filtered, and the filtrate was condensed to obtain a yellow liquid. The yellow liquid was purified by column chromatography (toluene:heptane=1:4) and recrystallized with chloroform/methanol. As a result, 0.39 g (yield: 30%) of yellow crystals A3 were obtained.

The emission spectrum of a $1 \times 10^{-5}$ mol/L toluene solution of Example Compound A3 was taken with F-4500 produced by Hitachi Corporation at an excitation wavelength of 350 nm by measuring the photoluminescence. A spectrum having the maximum intensity at 485 nm was obtained as a result.

Example 3

Synthesis of Example Compound A5

A5 was obtained by the same reactions and purification method as those of Example 1 except that the organic compound E2 used in Example 1 was changed to E15.

[Chem. 20]

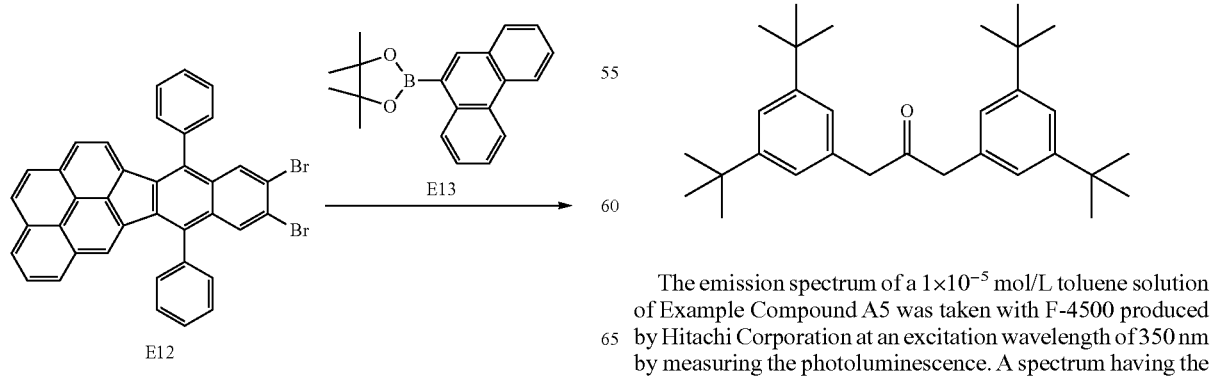

The emission spectrum of a $1 \times 10^{-5}$ mol/L toluene solution of Example Compound A5 was taken with F-4500 produced by Hitachi Corporation at an excitation wavelength of 350 nm by measuring the photoluminescence. A spectrum having the maximum intensity at 488 nm was obtained as a result.

Example 4

Synthesis of Example Compound A10

A10 was obtained by the same reactions and purification method as those of Example 1 except that the organic compound E2 used in Example 1 was changed to E15 and 1-pyreneboronic acid was changed to E16.

[Chem. 21]

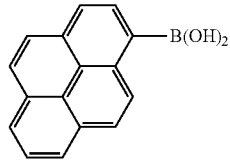

E16

The emission spectrum of a $1 \times 10^{-5}$ mol/L toluene solution of Example Compound A10 was taken with F-4500 produced by Hitachi Corporation at an excitation wavelength of 350 nm by measuring the photoluminescence. A spectrum having the maximum intensity at 490 nm was obtained as a result.

Example 5

Synthesis of Example Compound A11

A11 was obtained by the same reactions and purification method as those of Example 1 except that the organic compound E1 used in Example 1 was changed to E17 and 1-pyreneboronic acid was changed to E16.

[Chem. 22]

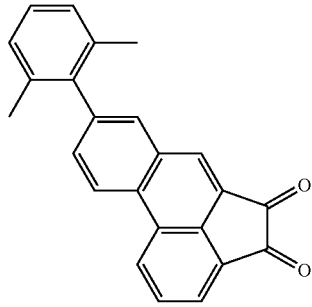

E17

The emission spectrum of a $1 \times 10^{-5}$ mol/L toluene solution of Example Compound A11 was taken with F-4500 produced by Hitachi Corporation at an excitation wavelength of 350 nm by measuring the photoluminescence. A spectrum having the maximum intensity at 490 nm was obtained as a result.

Example 6

Synthesis of Example Compound A26

A26 was obtained by the same reactions and purification method as those of Example 2 except that the organic compound E9 used in Example 2 was changed to E18.

[Chem. 23]

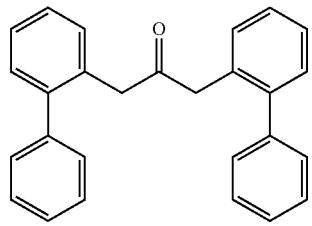

E18

The emission spectrum of a $1 \times 10^{-5}$ mol/L toluene solution of Example Compound A26 was taken with F-4500 produced by Hitachi Corporation at an excitation wavelength of 350 nm by measuring the photoluminescence. A spectrum having the maximum intensity at 488 nm was obtained as a result.

Examples 7 to 12

In Examples 7 to 12, multilayer organic light-emitting devices having the anode/hole transport layer/emission layer/hole-exciton blocking layer/electron transport layer/cathode structure were fabricated. An ITO film 100 nm in thickness on a glass substrate was patterned and the following organic layers and electrode layers were continuously formed by vacuum vapor deposition under resistive heating in a $10^{-5}$ Pa vacuum chamber on the ITO substrate while adjusting the electrode area of the opposing electrodes to 3 mm$^2$:

Hole transport layer (40 nm) G-1
Emission layer (30 nm)
  Host G-2
  Guest: Example Compound (weight ratio: 5%)
Hole-exciton blocking layer (10 nm) G-3
Electron transport layer (30 nm) G-4
Metal electrode layer 1 (1 nm) LiF
Metal electrode layer 2 (100 nm) Al

[Chem. 24]

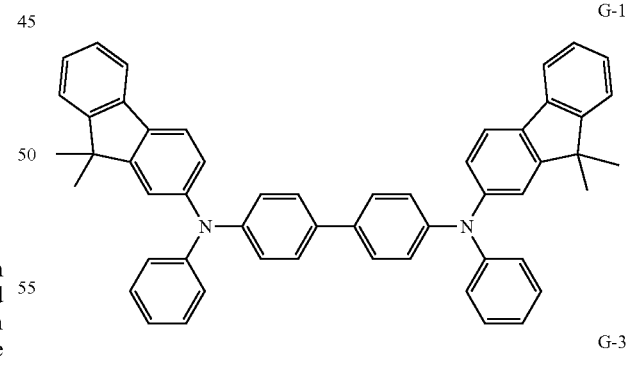

-continued

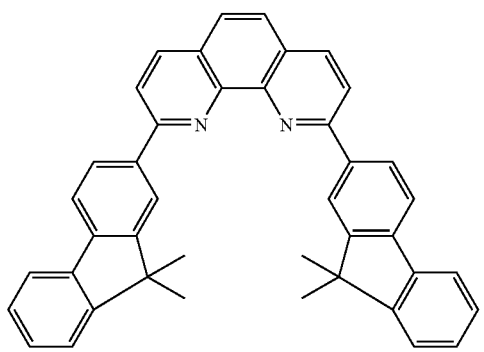

G-4

The characteristics of the organic light-emitting devices were measured with a pA meter 4140B produced by Hewlett-Packard Company, and the luminance was measured with BM7 produced by Topcon Corporation.

Emission efficiency and voltage of Examples 7 to 12 are shown in Table 4.

TABLE 4

|  | Guest | G-2 | Emission efficiency (cd/A) | Voltage (V) |
| --- | --- | --- | --- | --- |
| Example 7 | A2 | H8 | 14.5 | 3.3 |
| Example 8 | A5 | H6 | 15.0 | 3.2 |
| Example 9 | A5 | H21 | 14.6 | 3.2 |
| Example 10 | A10 | H21 | 14.7 | 3.3 |
| Example 11 | A11 | H9 | 15.1 | 3.4 |
| Example 12 | A26 | H15 | 15.0 | 3.6 |

Examples 13 to 17

In Examples 13 to 17, multilayer organic light-emitting device having an anode/hole transport layer/emission layer/electron transport layer/electron injection layer/cathode structure were fabricated.

The organic light-emitting devices had a resonance structure and were made by the following process.

An aluminum alloy (AlNd) film, i.e., a reflective anode, 100 nm in thickness was sputter-deposited on a glass substrate functioning as a support. Indium tin oxide was sputter-deposited thereon to form a transparent anode having a thickness of 80 nm. A device isolation film composed of polyimide is formed to a thickness of 1.5 µm around the anode, and an opening having a radius of 3 mm was formed. The resulting structure was ultrasonically washed with acetone and then isopropyl alcohol (IPA), washed with boiling IPA, and dried. The substrate surface was then subjected to UV cleaning.

The following organic layers were continuously formed by vacuum vapor deposition under resistive heating in a $10^{-5}$ Pa vacuum chamber. Then IZO was sputter-deposited to form a transparent electrode 30 nm in thickness functioning as a cathode. The resulting structure was sealed in a nitrogen atmosphere.

Layers constituting the organic light-emitting device were as follows:
Hole injection layer (135 nm) G-11
Hole transport layer (10 nm) G-12
Emission layer (35 nm)
  Host G-13
  Guest: Example Compound (weight ratio: 2%)
Electron transport layer (10 nm) G-14
Electron injection layer (70 nm) G-15 (weight ratio: 80%) and Li (weight ratio: 20%)

[Chem. 25]

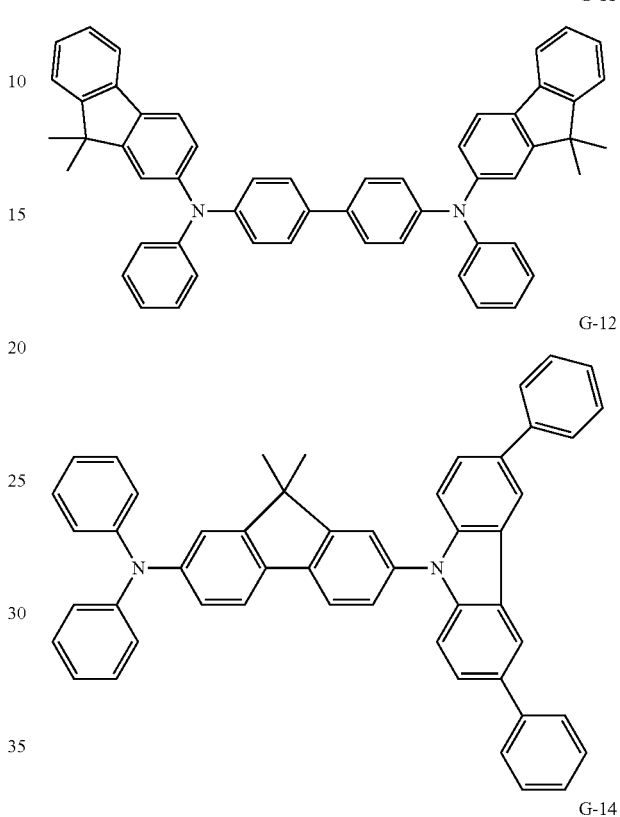

The characteristics of the organic light-emitting devices were measured with a pA meter 4140B produced by Hewlett-Packard Company, and the luminance was measured with BM7 produced by Topcon Corporation.

Emission efficiency and voltage of Examples 13 to 17 are shown in Table 5.

TABLE 5

| | Guest | G-2 | Emission efficiency (cd/A) | Voltage (V) |
|---|---|---|---|---|
| Example 13 | A2 | H9 | 24.6 | 3.7 |
| Example 14 | A5 | H4 | 24.8 | 3.9 |
| Example 15 | A10 | H22 | 24.8 | 4.0 |
| Example 16 | A11 | H7 | 25.0 | 4.1 |
| Example 17 | A26 | H7 | 24.7 | 3.8 |

Results and Considerations

The organic compound according to the present invention is a novel compound having a high quantum yield and emission suitable for green. When the organic compound is used in an organic light-emitting device, good emission characteristics can be attained.

As has been discussed with reference to the embodiments and examples, the organic compound according to the present invention can achieve emission in the green region because of the basic skeleton itself. The basic skeleton can provide a novel organic compound having a wide bandgap and a deep LUMO. Introduction of a substituent into the basic skeleton provides a novel organic compound capable of emitting not only green light but also red light. An organic light-emitting device including the novel organic compound can also be provided.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-115492, filed May 19, 2010, which is hereby incorporated by reference herein in its entirety.

The invention claimed is:

1. An organic compound represented by general formula (1)

[Chem. 1]

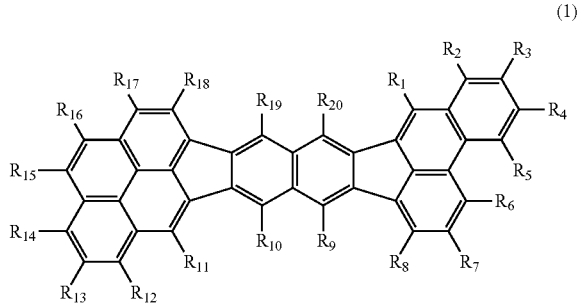

(1)

wherein $R_1$ to $R_{20}$ are each independently selected from the group consisting of a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group, and substituents of the alkyl group, the alkoxy group, the amino group, the aryl group, and the heterocyclic group are each individually selected from the group consisting of an alkyl group, an aralkyl group, an aryl group, a heterocyclic group, an amino group, an alkoxyl group, and a halogen atom.

2. The organic compound according to claim 1, wherein $R_1$ to $R_{20}$ are each independently selected from the group consisting of the hydrogen atom, the substituted or unsubstituted alkyl group, and the substituted or unsubstituted aryl group.

3. The organic compound according to claim 2, wherein at least one of $R_9$, $R_{10}$, $R_{19}$, and $R_{20}$ is the substituted or unsubstituted aryl group.

4. An organic light-emitting device comprising:
a cathode;
an anode; and
an organic compound layer interposed between the cathode and the anode,
wherein at least one layer in the organic compound layer contains the organic compound according to claim 1.

5. The organic light-emitting device according to claim 4, wherein the organic compound layer is an emission layer.

6. An image display apparatus comprising:
a plurality of pixels, each pixel including the organic light-emitting device according to claim 4 and a thin film transistor configured to control a luminance of the organic light-emitting device.

7. An imaging apparatus comprising:
a display unit; and
an imaging unit,
wherein the display unit includes a plurality of pixels;
each pixel includes the organic light-emitting device according to claim 4 and a thin film transistor configured to control a luminance of the organic light-emitting device; and
the imaging unit includes an imaging optical system.

8. An image-forming apparatus comprising:
an exposure light switch which has the organic light-emitting device according to claim 4.

9. A lighting apparatus comprising:
the organic light-emitting device according to claim 4.

* * * * *